(12) United States Patent
Tavana

(10) Patent No.: US 10,777,324 B2
(45) Date of Patent: Sep. 15, 2020

(54) ENGINEERED 3D LUNG AIRWAY TREE

(71) Applicant: Hossein Tavana, Hudson, OH (US)

(72) Inventor: Hossein Tavana, Hudson, OH (US)

(73) Assignee: The University of Akron, Akron, OH (US)

(*) Notice: Subject to any disclaimer, the term of this patent is extended or adjusted under 35 U.S.C. 154(b) by 404 days.

(21) Appl. No.: 15/802,964

(22) Filed: Nov. 3, 2017

(65) Prior Publication Data

US 2018/0121627 A1 May 3, 2018

Related U.S. Application Data

(60) Provisional application No. 62/416,975, filed on Nov. 3, 2016.

(51) Int. Cl.
*G16H 50/50* (2018.01)
*A61B 34/10* (2016.01)
*A61M 16/00* (2006.01)
*G06T 19/00* (2011.01)
*B33Y 50/00* (2015.01)
*B33Y 80/00* (2015.01)
(Continued)

(52) U.S. Cl.
CPC ............. *G16H 50/50* (2018.01); *A61B 34/10* (2016.02); *A61M 16/021* (2017.08); *B29C 64/124* (2017.08); *B33Y 50/00* (2014.12); *B33Y 80/00* (2014.12); *G06T 19/00* (2013.01); *A61B 2034/105* (2016.02); *B29C 64/165* (2017.08); *B33Y 50/02* (2014.12); *G06F 30/00* (2020.01); *G06T 7/0012* (2013.01)

(58) Field of Classification Search
CPC ............. A61B 2034/105; A61B 34/10; A61M 16/021; B29C 64/124; B29C 64/165; B33Y 50/00; B33Y 50/02; B33Y 80/00; G06F 17/50; G06T 19/00; G06T 7/0012; G16H 50/50
See application file for complete search history.

(56) References Cited

U.S. PATENT DOCUMENTS 6,083,162 A 7/2000 Vining
6,901,277 B2 5/2005 Kaufman et al.
(Continued)

OTHER PUBLICATIONS

Rowe, Jacky A. Rosati, Ray Burton, George McGregor, Rob McCauley, Wei Tang, and Richard Spencer. "Development of a three-dimensional model of the human respiratory system for dosimetric use." Theoretical Biology and Medical Modelling 10, No. 1 (2013): 28.*

(Continued)

*Primary Examiner* — Aniss Chad
(74) *Attorney, Agent, or Firm* — Renner Kenner Greive Bobak Taylor & Weber

(57) ABSTRACT

A method of producing a model of a human lung includes preparing a computer file within a computer aided design system, mathematically slicing the computer file into a plurality of layers to produce a sliced computer file, providing the sliced computer file to an additive manufacturing apparatus, and fabricating, with the additive manufacturing apparatus, a 3D object based on the sliced computer file. The model of the human lung may be utilized to evaluate surfactant treatment, to improve subsequent surfactant administration to a human patient.

18 Claims, 11 Drawing Sheets

(51) Int. Cl.
  *B29C 64/124* (2017.01)
  *B33Y 50/02* (2015.01)
  *B29C 64/165* (2017.01)
  *G06T 7/00* (2017.01)
  *G06F 30/00* (2020.01)

(56) References Cited

U.S. PATENT DOCUMENTS

| | | | |
|---|---|---|---|
| 6,909,913 | B2 | 6/2005 | Vining |
| 7,715,608 | B2 | 5/2010 | Vaz et al. |
| 8,579,620 | B2 | 11/2013 | Wu |
| 9,697,639 | B2 | 7/2017 | Masumoto |
| 2011/0093243 | A1* | 4/2011 | Tawhai ............ G06T 7/0012 703/2 |
| 2015/0282887 | A1* | 10/2015 | Yamada ............ G06T 19/003 600/410 |
| 2016/0005162 | A1* | 1/2016 | Markov ............ G06T 7/11 382/128 |
| 2016/0005163 | A1* | 1/2016 | Markov ............ G06T 7/11 382/128 |
| 2016/0005236 | A1* | 1/2016 | Lachmanovich ... G06F 3/04815 345/419 |
| 2017/0182708 | A1* | 6/2017 | Lin ............ B33Y 10/00 |
| 2017/0217102 | A1 | 8/2017 | Mansi et al. |

OTHER PUBLICATIONS

Wilson, C. A., O. J. Arthurs, A. E. Black, S. Schievano, C. Hunt, S. van Hoog, C. Wallis, and M. R. J. Sury. "Printed three-dimensional airway model assists planning of single-lung ventilation in a small child." BJA: British Journal of Anaesthesia 115, No. 4 (2015): 616-620.*

Sauret et al, Study of the three-dimensional geometry of the central conducting airways in man using computed tomographic (CT) images, J. Anat. (2002), 200, pp. 123-134.

Tavana et al, Epithelium damage and protection during reopening of occluded airways in a physiologic microfluidic pulmonary airway model, Biomed Microdevices (2011) 13:731-742.

Raabe et al, Tracheobronchial Geometry: Human, Dog, Rat, Hamster—A Compilation o f Selected Data From the Project Respiratory Tract Deposition Models, Inhalation Toxicology Research Institute, Mar. 1976.

Kitaoka et al, A three-dimensional model of the human airway tree, J Appl Physiol 87:2207-2217, 1999.

Phalen et al, Application of an Idealized Model to Morphometry of the Mammalian Tracheobronchial Tree, Anat. Rec. (1978)1 90: 167-176.

Weibel et al, Architecture of the Human Lung, Science, New Series, vol. 137, No. 3530. (Aug. 24, 1962), pp. 577-585.

* cited by examiner

ENGINEERED 3D LUNG AIRWAY TREE

CROSS-REFERENCE TO RELATED APPLICATIONS

The present application claims the benefit of U.S. Provisional Patent Application No. 62/416,975, filed Nov. 3, 2016, which is incorporated herein by reference.

FIELD OF THE INVENTION

The present invention relates to computational modeling of a lung airway tree. The present invention further relates to 3D printing a model lung airway tree based on the computational modeling.

BACKGROUND OF THE INVENTION

The lungs are vital for various functions such as metabolism, secretion of substances including mucus and surfactant, and filtering of undesirable materials. Their main function is gas exchange to enable blood oxygenation and removal of carbon dioxide. The lungs house pulmonary airways that consist of a network of continuously-branching tubes which become shorter, narrower, and more numerous as they penetrate deeper into the lungs. The trachea (windpipe) is the main access point to transport air to and from the lungs. The trachea then splits into the left and right primary bronchi (generation one airways), each of which subsequently divides into two secondary bronchi.

Delivery of therapeutic fluids, such as surfactant solutions, into lungs is a major strategy to treat various respiratory disorders. Instilled solutions form liquid plugs in lung airways, e.g. in the trachea or primary bronchi. The plugs propagate downstream in airways by inspired air or forced ventilation, continuously split at airway bifurcations to smaller daughter plugs and simultaneously lose mass from their trailing menisci, and eventually rupture. A uniform distribution of the instilled liquid in lung airways is essential for increasing the treatments success. The uniformity of distribution of instilled liquid in the lungs greatly depends on the splitting of liquid plugs between daughter airways, especially in the first few generations of airways from which airways of different lobes of lungs emerge.

U.S. Pub. No. 2011/0093243 discloses creating a computational fluid dynamics mesh. A set of images is obtained, representing the branching biological structure, such as airways within a lung. The center line locations and measurements of airway diameter from the images, including estimated diameters for the one dimensionally modeled airways, is used to create an initial estimation of a branching mesh. Aspects of the image are analyzed to extract information defining one or more surfaces. Branching passageways can be determined in part with reference to structures that can be discerned and in part are inferred from predetermined relationships forming a model. Notably, the mesh is only provided for computational fluid dynamic (CFD) analysis and the '243 publication appears to lack the ability to produce a 3D object.

There remains a need in the art for rational design of improved lung airway models in order to help elucidate delivery conditions that improve uniformity of distribution of instilled therapeutic liquids, such as surfactants, in the lungs. Availability of model airway trees is essential for progress in this area.

SUMMARY OF THE INVENTION

In a first embodiment, the present invention provides a method of producing a model of a human lung comprising steps of preparing a computer file within a computer aided design system utilizing steps of forming a trachea portion having a first end and a second end, forming a first bifurcation zone at the second end of the trachea portion, the first bifurcation zone having a first branch and a second branch, extending a first generation bronchi tube from the first branch of the first bifurcation zone, the first generation bronchi tube having a distal end, forming a subsequent bifurcation zone at the distal end of the first generation bronchi tube, which may be characterized as a prior generation bronchi tube, the subsequent bifurcation zone having a first branch and a second branch, extending a subsequent generation bronchi tube from the first branch of the subsequent bifurcation zone, which may be characterized as a prior bifurcation zone, the subsequent generation bronchi tube having a distal end, repeating the steps of forming a subsequent bifurcation zone at the distal end of the prior generation bronchi tube, the subsequent bifurcation zone having a first branch and a second branch, and extending a subsequent generation bronchi tube from the first branch of the prior bifurcation zone, until a predetermined number of generations of bronchi tubes have been formed, mathematically slicing the computer file into a plurality of layers to produce a sliced computer file, providing the sliced computer file to an additive manufacturing apparatus, fabricating, with the additive manufacturing apparatus, a 3D object based on the sliced computer file.

In a second embodiment, the present invention provides a method as in any of the above embodiments, wherein at least a third generation bronchi tube is formed, wherein the third generation bronchi tube is rotated 90°, or approximate thereto, in the 3D space with respect to the prior generation bronchi tube.

In a third embodiment, the present invention provides a method as in any of the above embodiments, wherein the predetermined number of bronchi tubes is greater than three, wherein the third generation bronchi tube and each subsequent generation bronchi tube is rotated 90°, or approximate thereto, in the 3D space with respect to the prior generation bronchi tube.

In a fourth embodiment, the present invention provides a method as in any of the above embodiments, the trachea portion having a sidewall with a thickness, wherein the step of forming a trachea portion includes steps of forming the first end as a circle having a predetermined interior diameter, prescribing a length of the trachea portion as five times the interior diameter of the first end, prescribing a fixed tapering amount for the entire model, which is characterized by a decrease from the interior diameter of the first end to an interior diameter of the second end, prescribing a thickness of the sidewall, wherein the steps of prescribing thereby set the length of the trachea portion, the interior diameter of the second end, the thickness of the sidewall, to thereby allow the trachea portion to be formed within the computer aided design system.

In a fifth embodiment, the present invention provides a method as in any of the above embodiments, wherein the step of forming a first bifurcation zone includes steps of extending two construction lines from the second end of the trachea portion, where the two construction lines form a total bifurcation angle, extending a perpendicular construction line from a point on each of the two construction lines, each of the perpendicular construction lines extending inward until meeting at a point, dimensioning one of the perpendicular construction lines based on a predetermined value for a radius of the first generation bronchi tube to form a dimensioned perpendicular construction line, and forming a plane along the dimensioned perpendicular construction line.

In a sixth embodiment, the present invention provides a method as in any of the above embodiments, wherein the step of extending a first generation bronchi tube includes steps of forming a first circle having a predetermined diameter along the plane along the dimensioned perpendicular construction line, dimensioning one of the construction lines, starting from the point on the construction line and based on a predetermined value for a length of the first generation bronchi tube, to thereby form a dimensioned construction line having a distal point, forming a plane along the distal point of dimensioned construction line, and forming a second circle having a predetermined diameter along the plane along the distal point of dimensioned construction line.

In a seventh embodiment, the present invention provides a method as in any of the above embodiments, wherein the length of the first generation bronchi tube is three times the diameter of the first circle.

In an eighth embodiment, the present invention provides a method as in any of the above embodiments, wherein the fixed tapering amount is 13.5% percent such that the diameter of the second circle having a predetermined diameter is a 13.5% decrease compared to the diameter of the first circle having a predetermined diameter.

In a ninth embodiment, the present invention provides a method as in any of the above embodiments, wherein the diameter of the first end of a particular generation bronchi tube is characterized by $d_z=d_0 \times 2^{-z/3}$, where z is the generation number and $d_0$ is the diameter of the first end of the trachea portion.

In a tenth embodiment, the present invention provides a method as in any of the above embodiments, wherein the predetermined number of generations of bronchi tubes is characterized by n, wherein, after the predetermined number of generations of bronchi tubes have been formed, the step of preparing a computer file further comprises steps of separating the trachea portion and the first bifurcation zone from the first generation bronchi tube to form a trachea portion and first bifurcation zone part and a first generation bronchi tube through n generation bronchi tube part, saving the trachea portion and the first bifurcation zone as a part within computer aided design system, saving the first generation bronchi tube through n generation bronchi tube part as a part within computer aided design system, separating the first generation bronchi tube and the subsequent bifurcation zone from the subsequent generation bronchi tube to form a subsequent generation bronchi tube through n generation bronchi tube part, saving the subsequent generation bronchi tube through n generation bronchi tube part as a part within computer aided design system, adding the saved first generation bronchi tube through n generation bronchi tube part to the second branch of the first bifurcation zone, and adding the saved subsequent generation bronchi tube through n generation bronchi tube part to the second branch of the subsequent bifurcation zone.

In an eleventh embodiment, the present invention provides a method as in any of the above embodiments, wherein the 3D object is transparent.

In a twelfth embodiment, the present invention provides a method as in any of the above embodiments, wherein the additive manufacturing apparatus is a stereolithographic system.

In a thirteenth embodiment, the present invention provides a method as in any of the above embodiments, wherein the 3D object is made from an (acrylonitrile butadiene styrene)-like photopolymer.

In a fourteenth embodiment, the present invention provides a method as in any of the above embodiments, wherein the computer aided design system is SOLIDWORKS.

In a fifteenth embodiment, the present invention provides a method as in any of the above embodiments, wherein the total bifurcation angle is 80°, or approximate thereto.

In a sixteenth embodiment, the present invention provides a method as in any of the above embodiments, further comprising the step of injecting a surfactant into the 3D object to thereafter analyze the flow of the surfactant through the 3D object.

BRIEF DESCRIPTION OF THE DRAWINGS

Advantages of the present invention will become better understood with regard to the following description, appended claims, and accompanying drawings wherein:

DETAILED DESCRIPTION OF ILLUSTRATIVE EMBODIMENTS

Figure 1:
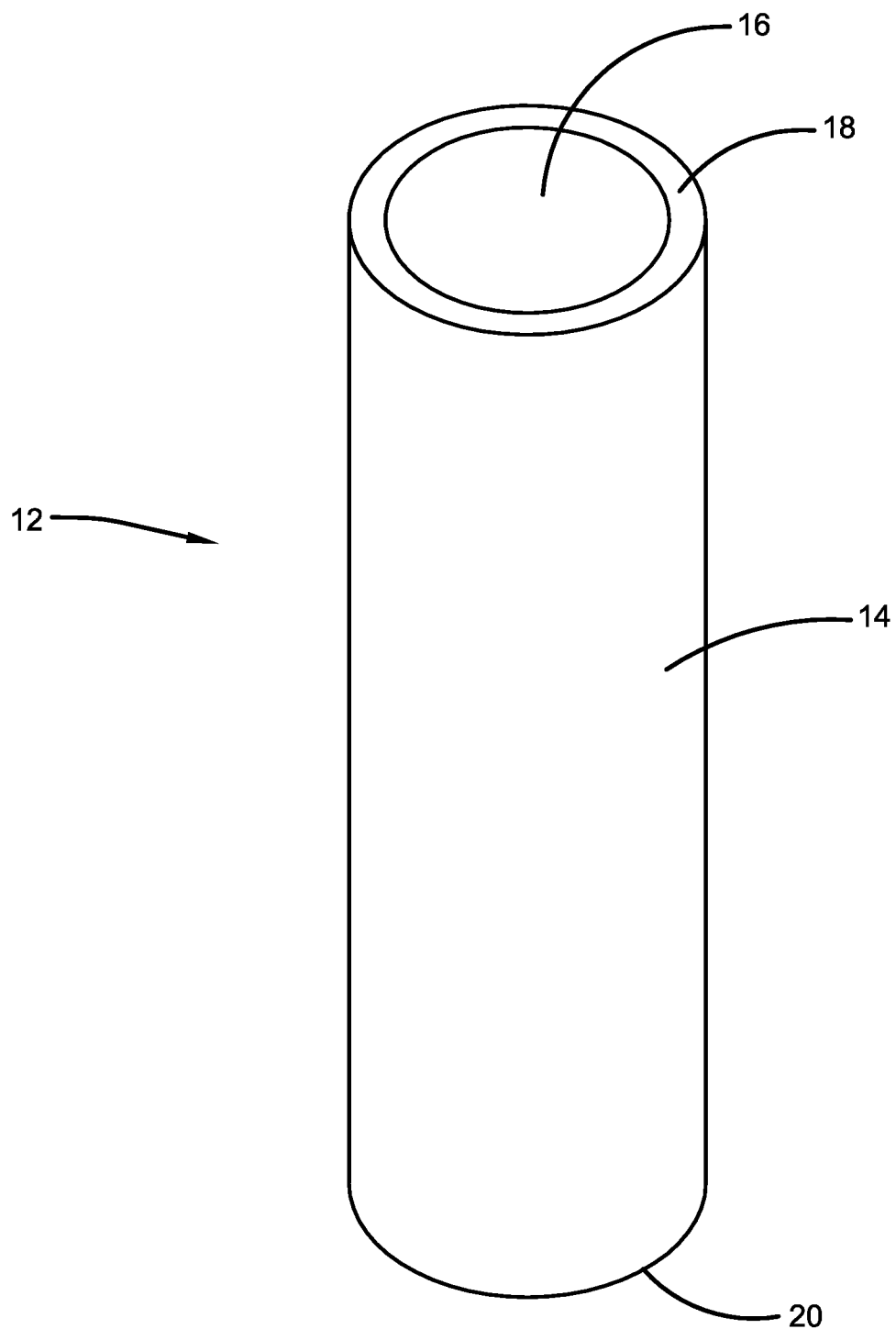
FIG. 1 is a schematic showing a tapered tube to model a trachea.

With reference to the Figures, one or more embodiments of the invention provide a biomimetic, symmetrical model of a lung, generally indicated by the numeral 10. Model 10 includes a trachea portion 12, which includes a longitudinal wall 14, which may also be referred to as a sidewall 14, and a hollow interior 16, which may also be referred to as an airway path 16, which is enclosed by longitudinal wall 14. Longitudinal wall 14 includes a circular first end 18, which serves as the initial entryway of model 10 for one or more fluids (e.g. air, therapeutic fluid). From first end 18, longitudinal wall 14 extends to a circular second end 20, which may be described as a distal end 20. Longitudinal wall 14 may extend in a tapered manner, with circular first end 18 having a slightly larger interior diameter than the interior diameter of circular second end 20. This tapering, and the tapering of additional generations of the model, disclosed elsewhere herein, allows for a smooth transition from one generation to the next generation. This may be described as model 10 having a continuous taper. This continuous taper is intended to match the continuous tapering present in human lungs.

The size of model 10 and one or more components thereof may be designed to model the size of a human lung. Parameters that collectively define the geometry of airways are tapering, diameter, length, thickness, and bifurcation angle for a pair of airways. The numeric value for one or more of these parameters may be selected based on modeling a human lung. The numeric value for one or more of these parameters may be selected based on data obtained from the lung of a particular individual, such as through CT imaging.

The tapering may be defined in terms of a percent decrease of the interior diameter of circular second end 20 compared to the interior diameter of circular first end 18. That is, the diameter of second end 20 is smaller than the diameter of first end 18, and longitudinal wall 14 gradually and consistently tapers in accord with the diameters. In one or more embodiments, the interior diameter of circular second end 20 is a 13.5% decrease, or approximate thereto, compared to the interior diameter of circular first end 18. In one or more embodiments, the interior diameter of circular second end 20 is a decrease in a range of from 10% to 15%, in other embodiments, from 13% to 14%, compared to the interior diameter of circular first end 18.

In one or more embodiments, the interior diameter of circular first end 18 is sized to model an adult trachea. In one or more embodiments, the interior diameter of circular first end 18 is 3.5 millimeters (mm), or approximate thereto, to model an infant trachea. In one or more embodiments, the interior diameter of circular first end 18 is in a range of from 2 mm to 5 mm, and in other embodiments, from 3 mm to 4 mm.

In one or more embodiments, the interior diameter of circular second end 20 is sized to model an infant trachea. In one or more embodiments, the interior diameter of circular second end 20 is sized to model an adult trachea. In one or more embodiments, the interior diameter of circular second end 20 is in a range of from 1.7 mm to 4.3 mm, and in other embodiments, from 2.6 mm to 3.5 mm.

In one or more embodiments, the length of longitudinal wall 14 is sized to model an adult trachea. In one or more embodiments, the length of longitudinal wall 14 is 17.5 millimeters, or approximate thereto, to model an infant trachea. In one or more embodiments, the length of longitudinal wall 14 is in a range of from 15 mm to 20 mm, and in other embodiments, from 17 mm to 18 mm. In one or more embodiments, the length of longitudinal wall 14 is in a range of from 12 mm to 22 mm, and in other embodiments, from 15 mm to 25 mm.

In one or more embodiments, the thickness of longitudinal wall 14 is sized to model an infant trachea. In one or more embodiments, the thickness of longitudinal wall 14 is sized to model an adult trachea. In one or more embodiments, the thickness of longitudinal wall 14 is 500 micrometers (µm), or approximate thereto. In one or more embodiments, the thickness of longitudinal wall 14 is in a range of from 300 µm to 700 µm, and in other embodiments, from 400 µm to 600 µm. In one or more embodiments, the thickness of longitudinal wall 14 is in a range of from 450 µm to 550 µm. In one or more embodiments, the thickness of longitudinal wall 14 is in a range of from 500 µm to 700 µm. The minimal thickness of longitudinal wall 14 and other components of model 10 may be determined by the method of fabricating model 10. That is, certain methods of fabrication and materials utilized to make model 10 may allow for thinner thickness than other methods and materials.

Figure 3:
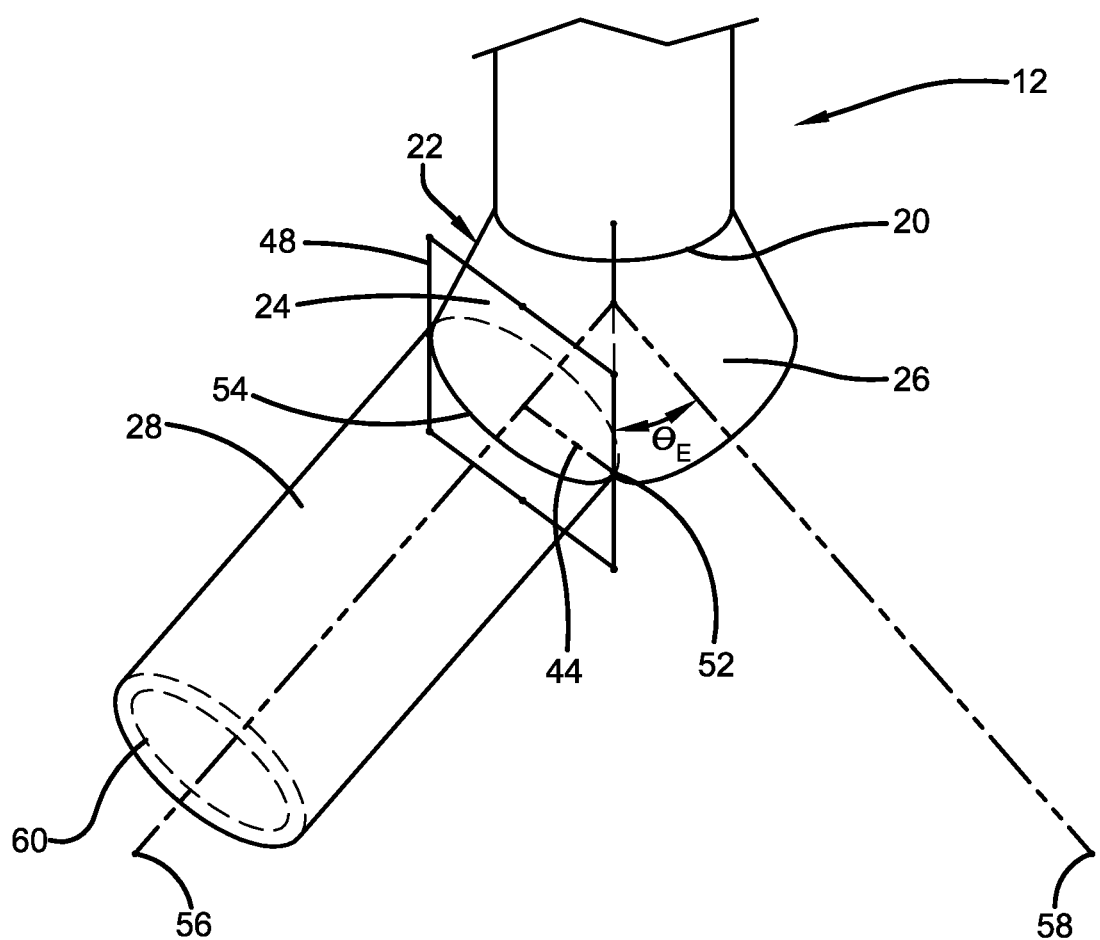
FIG. 3 is a schematic showing a bifurcation zone having a daughter tube from one of the bifurcation divisions, for a symmetrical model.
Figure 4:
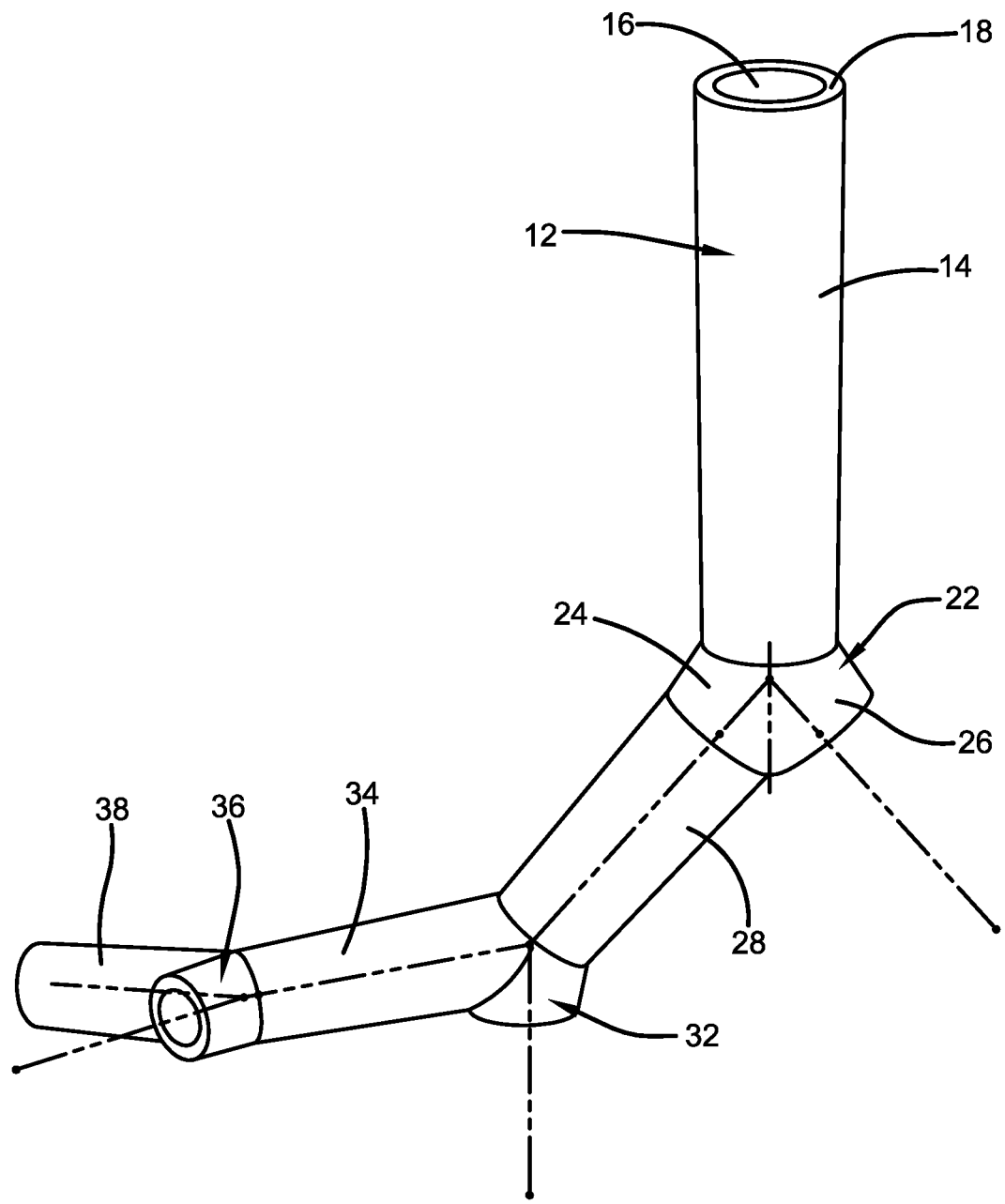
FIG. 4 is a schematic showing tubing of a third generation partial model, for a symmetrical model.

Trachea portion 12 may be said to be a generation zero (z=0) for model 10. For providing additional generations, trachea portion 12 extends into a first bifurcation 22 having a first branch 24 and a second branch 26 from which a first bronchi portion 28 and a second bronchi portion 30 respectively extend. First bronchi portion 28 and a second bronchi portion 30 may be described as daughter airways or first generation bronchi portions. For symmetrical model 10, first branch 24 and second branch 26 are formed at equal angles, represented by $\theta_E$ in FIG. 3, where the angles are with respect to the position of trachea portion 12. In one or more embodiments, $\theta_E$ is 40°, or approximate thereto. In one or more embodiments, $\theta_E$ is in a range of from 35° to 45°, in other embodiments, from 38° to 42°. Though only shown for first generation bronchi portions, for symmetrical model 10, each pair of subsequent generation bronchi portions are also provided at the same equal angle, $\theta_E$.

Each bronchi portion includes a longitudinal wall, which may also be referred to as a sidewall, and a hollow interior, which may also be referred to as an airway path. A first end of each bronchi portion is coupled with the respective branch of the bifurcation, with longitudinal wall extending from the first end to a second end. The second end may be described as a distal end.

Figure 7:
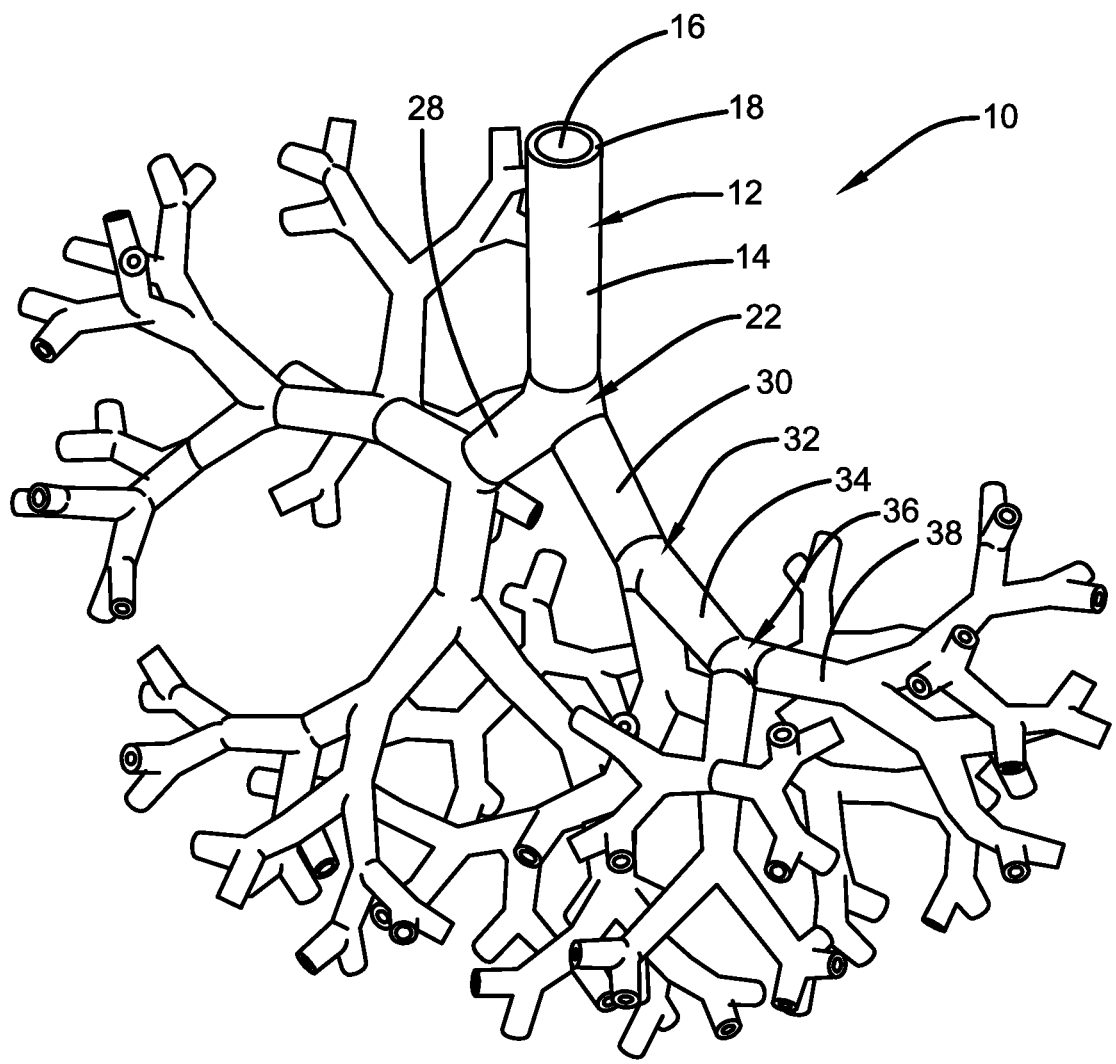
FIG. 7 is a schematic showing a seventh generation, symmetrical model.
Figure 8:
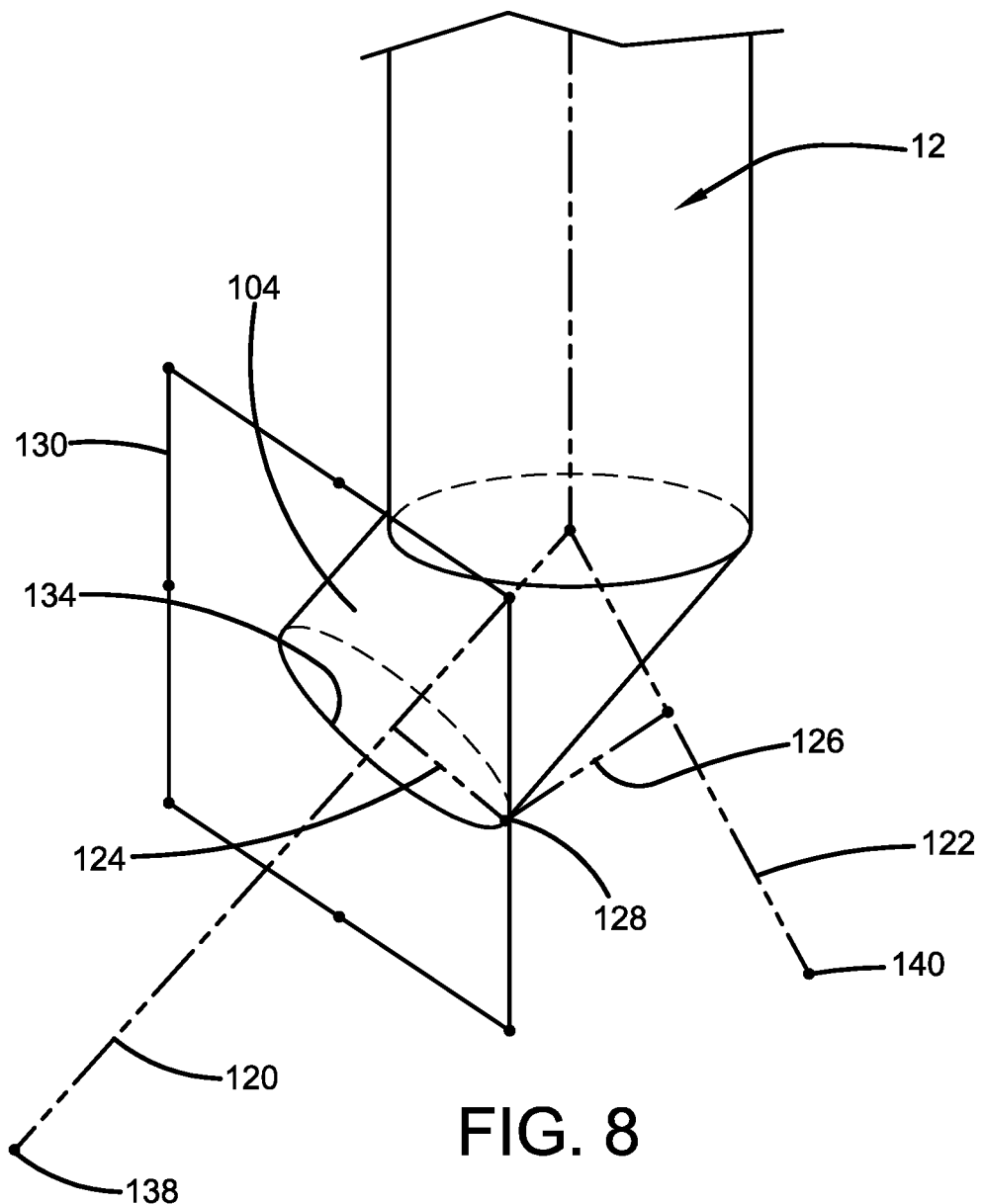
FIG. 8 is a schematic showing a plane in which a first generation daughter tube will be formed, for an asymmetrical model.

Each of the first generation bronchi portions 24, 26 extends to an additional bifurcation 32 to provide second generation bronchi portions 34. In the same manner, each second generation bronchi portion 34 extends to an additional bifurcation 36 to provide third generation bronchi portions 38, and so on, up to a desired amount of generations of bronchi portions. Model 10 may include any suitable number of generations of bronchi portions. In one or more embodiments, model 10 includes seven generations of bronchi portions, as shown in FIG. 7. In one or more embodiments, model 10 includes sixteen generations of bronchi portions to model an infant trachea. In one or more embodiments, model 10 includes twenty-three generations of bronchi portions to model an adult trachea.

In one or more embodiments, the interior diameter, length, and wall thickness of the first generation bronchi portions, and each subsequent generation of bronchi portions, may be based on the size of trachea portion 12. For example, it is generally known in the art that there is a relationship between the diameter of a human trachea and the generation number of subsequent lung airways. In one or more embodiments, this relationship may be characterized as $d_z = d_0 \times 2^{-z/3}$, where z is the generation number, $d_z$ is the diameter of a lung airway of the z generation number, and $d_0$ is the trachea diameter. It is also generally known that the length of a human trachea is five times, or approximate thereto, the diameter of the airway. This relationship may therefore be characterized as $L_0 = 5d_0$. It is also generally known that the length of a subsequent generation human airway is three times, or approximate thereto, the diameter of the airway. This relationship may therefore be characterized as $L_z = 3d_z$.

In one or more embodiments, the tapering of the first generation bronchi portions, and each subsequent generation of bronchi portions may be defined in terms of a percent decrease from the interior diameter of the first end to the interior diameter of the second end. That is, the second end diameter is smaller than the first end diameter, and the wall gradually and consistently tapers in accord with the diameters. In one or more embodiments, the percent decrease of the interior diameter of the second end of the airways compared to the interior diameter of the first end of the airways is the same as the percent decrease of the interior diameter of second end 20 of trachea portion 12 to the interior diameter of first end 18 of trachea portion 12. That is, the tapering, or percent decrease may be a fixed number for each component of model 10.

In one or more embodiments, the interior diameter of the second end of the airways is a 13.5% decrease, or approximate thereto, compared to the interior diameter of the first end of the airways. In one or more embodiments, interior diameter of the second end of the airways is a decrease in a range of from 11% to 16%, in other embodiments, from 13% to 14%, compared to interior diameter of the first end of the airways.

Thus, in one or more embodiments, based on the above relationships between the diameter of trachea portion 12 and subsequent components, and assuming a fixed tapering for each component, selecting a desired diameter of first end 18 of trachea portion 12 will prescribe the remaining sizes (e.g. length of trachea portion 12, diameter of each subsequent generation bronchi portion, and length of each subsequent generation bronchi portion).

Subsequent generations of bronchi portions for model 10 may also be characterized by a rotation within the 3D space. This rotation may be provided in order to model the characteristics of a human lung. It is generally known in the art that starting at generation z=3, airways rotate 90°, or approximate thereto, in the 3D space with respect to the plane of their parent airway, and that this rotation continues for every subsequent generation thereafter. Anatomically, it is believed this rotation allows larger numbers of airways to fit in the chest cavity.

In one or more embodiments, generation z=3 of bronchi portions, rotates 90°, or approximate thereto, in the 3D space with respect to the plane of the generation z=2 of bronchi portions. This can be seen in FIG. 7 with the rotation of bifurcation 36 with respect to the plane of bronchi portion 34. In one or more embodiments, this rotation of 90°, or approximate thereto, continues for every subsequent generation of bronchi portions after z=3.

One or more embodiments of the invention provide an asymmetrical model of a lung, generally indicated by the numeral 100. Model 100 includes a trachea portion 12, similar to as described above for model 10. Similar to model 10, the size of model 100 and one or more components thereof may be designed to model the size of a human lung. Parameters that collectively define the geometry of airways are tapering, diameter, length, thickness, and bifurcation angle for a pair of airways. The numeric value for one or more of these parameters may be selected based on modeling a human lung. The numeric value for one or more of these parameters may be selected based on data obtained from the lung of a particular individual, such as through CT imaging.

Trachea portion 12 may be said to be a generation zero (z=0) for model 100. For providing additional generations, trachea portion 12 extends into a first bifurcation 102 having a first branch 104 and a second branch 106 from which a first bronchi portion 108 and a second bronchi portion 110 respectively extend. First bronchi portion 108 and a second bronchi portion 110 may be described as daughter airways or first generation bronchi portions.

Figure 9:
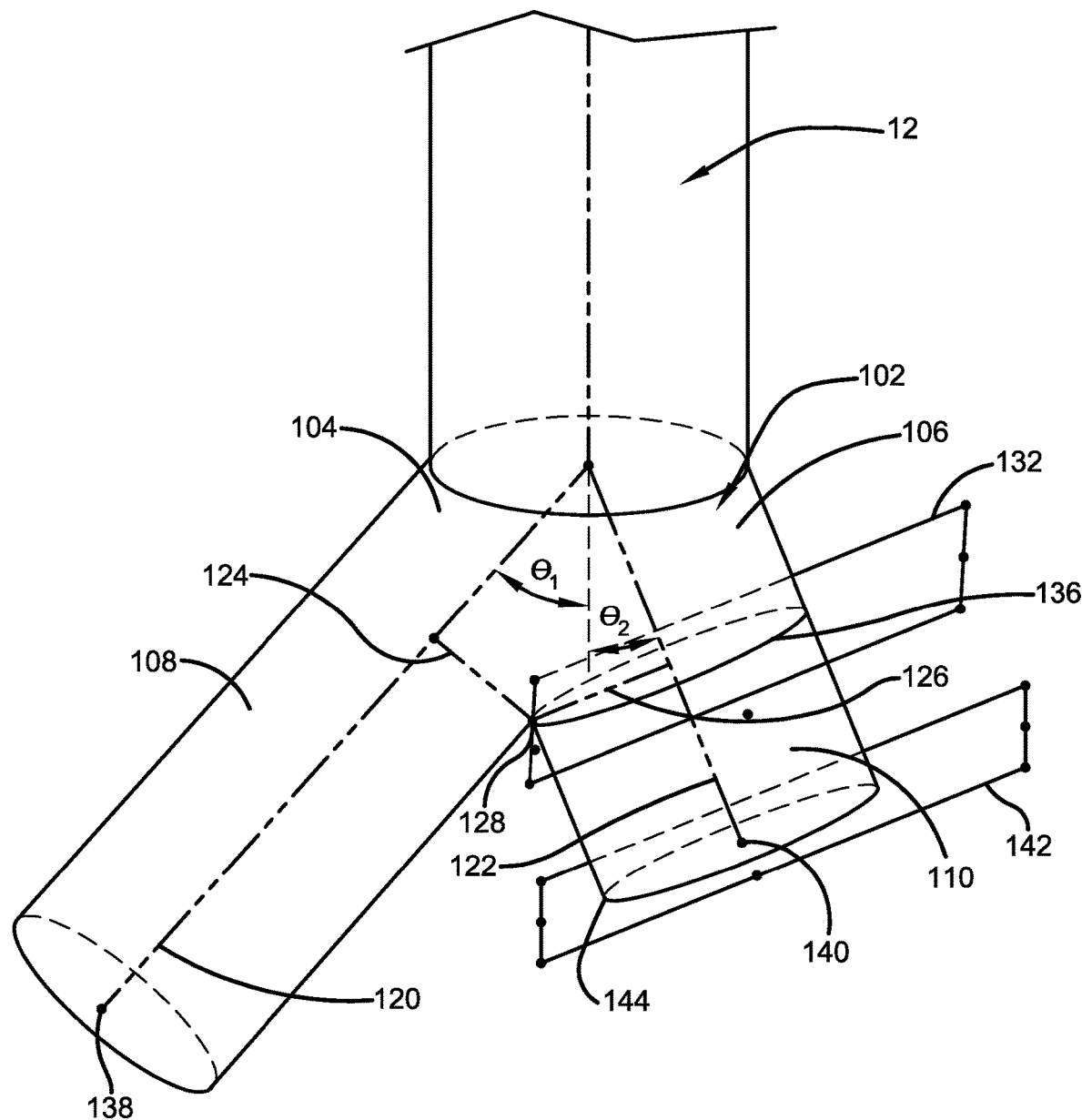
FIG. 9 is a schematic showing a bifurcation zone having first generation daughter tubes, for an asymmetrical model.

For asymmetrical model 100, first branch 104 and second branch 106 are formed at different angles, represented by $\theta_1$ and $\theta_2$ in FIG. 9, where the angles are with respect to the position of trachea portion 12. In one or more embodiments, $\theta_1$ is 40°, or approximate thereto. In one or more embodiments, $\theta_1$ is in a range of from 36° to 44°, in other embodiments, from 38° to 42°. In one or more embodiments, $\theta_2$ is 25°, or approximate thereto. In one or more embodiments, $\theta_2$ is in a range of from 21° to 29°, in other embodiments, from 23° to 27°.

Each pair of subsequent generation bronchi portions may also be provided at the above described angles, $\theta_1$ and $\theta_2$. In other embodiments, the subsequent generation bronchi portions are provided at angles different from $\theta_1$ and $\theta_2$.

In one or more embodiments, the sizing of asymmetrical model 100 may be based on previously developed models of human lungs. In one or more embodiments, bifurcation angles, $\theta_1$ and $\theta_2$ and bifurcation angles of daughter tubes and other sizing of asymmetrical model 100 (e.g. interior diameter, length, and wall thickness of bronchi portions, and interior diameter, length, and wall thickness of trachea portion) may be based on the human lung data obtained by Raabe et al. (TRACHEOBRONCHIAL GEOMETRY: HUMAN, DOG, RAT, HAMSTER—A Compilation of Selected Data From the Project Respiratory Tract Deposition Models; Inhalation Toxicology Research Institute; 1976), which is incorporated herein by reference.

In one or more embodiments, first bronchi portion 108 may have a sizing of 13.8 mm in diameter, or approximate thereto. In one or more embodiments, first bronchi portion 108 may have a sizing of 56.3 mm in length, or approximate thereto. As the smaller diameter bronchi portion, first bronchi portion 108 may be referred to as a minor daughter tube.

In one or more embodiments, second bronchi portion 110 may have a sizing of 17.5 mm in diameter, or approximate thereto. In one or more embodiments, second bronchi portion 110 may have a sizing of 30.9 mm in length, or approximate thereto. As the larger diameter bronchi portion, second bronchi portion 110 may be referred to as a major daughter tube.

Each bronchi portion includes a longitudinal wall, which may also be referred to as a sidewall, and a hollow interior, which may also be referred to as an airway path. A first end of each bronchi portion is coupled with the respective branch of the bifurcation, with longitudinal wall extending from the first end to a second end. The second end may be described as a distal end.

Figure 10:
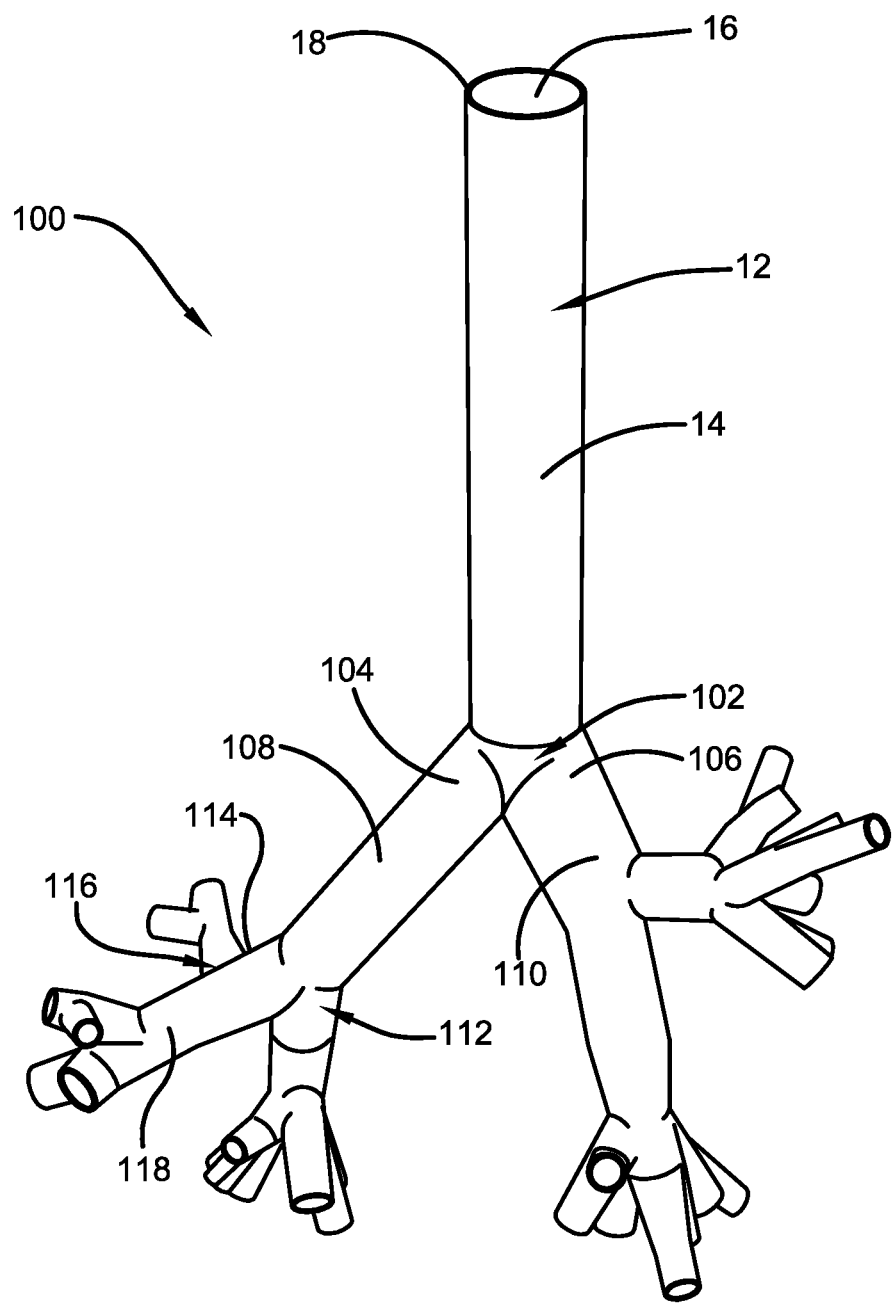
FIG. 10 is a schematic showing a fifth generation, asymmetrical model.

Each of the first generation bronchi portions 108, 110 extends to an additional bifurcation 112 to provide second generation bronchi portions 114. In the same manner, each second generation bronchi portion 114 extends to an additional bifurcation 116 to provide third generation bronchi portions 118, and so on, up to a desired amount of generations of bronchi portions. Model 100 may include any suitable number of generations of bronchi portions. In one or more embodiments, model 100 includes seven generations of bronchi portions, as shown in FIG. 10. In one or more embodiments, model 100 includes sixteen generations of bronchi portions to model an infant trachea. In one or more embodiments, model 100 includes twenty-three generations of bronchi portions to model an adult trachea.

In one or more embodiments, the tapering of the first generation bronchi portions, and each subsequent generation of bronchi portions may be defined in terms of a percent decrease from the interior diameter of the first end to the interior diameter of the second end. That is, the second end diameter is smaller than the first end diameter, and the wall gradually and consistently tapers in accord with the diameters. In one or more embodiments, the percent decrease of the interior diameter of the second end of the airways compared to the interior diameter of the first end of the airways is the same as the percent decrease of the interior diameter of second end 20 of trachea portion 12 to the interior diameter of first end 18 of trachea portion 12. That is, the tapering, or percent decrease may be a fixed number for each component of model 100.

In one or more embodiments, the interior diameter of the second end of the airways is a 13.5% decrease, or approximate thereto, compared to the interior diameter of the first end of the airways. In one or more embodiments, interior diameter of the second end of the airways is a decrease in a range of from 11% to 16%, in other embodiments, from 13% to 14%, compared to interior diameter of the first end of the airways.

In one or more embodiments, based on the above incorporated data from Raabe et al., selecting a desired size of trachea portion 12 will prescribe the remaining sizes (e.g. length of trachea portion 12, diameter of each subsequent generation bronchi portion, and length of each subsequent generation bronchi portion).

Subsequent generations of bronchi portions for model 100 may also be characterized by a rotation within the 3D space. This rotation may be provided in order to model the characteristics of a human lung. It is generally known in the art that starting at generation z=3, airways rotate 90°, or approximate thereto, in the 3D space with respect to the plane of their parent airway, and that this rotation continues for every subsequent generation thereafter. Anatomically, it is believed this rotation allows larger numbers of airways to fit in the chest cavity.

In one or more embodiments, generation z=3 of bronchi portions, rotates 90°, or approximate thereto, in the 3D space with respect to the plane of the generation z=2 of bronchi portions. This can be seen in FIG. 10 with the rotation of bifurcation 116 with respect to the plane of bronchi portion 114. In one or more embodiments, this rotation continues for every subsequent generation of bronchi portions after z=3.

Model 10 and model 100 may be developed by utilizing one or more known computer aided design systems, which may also be described as 3D modeling systems. This utilization of one or more known computer aided design systems may include preparing a computer file representative of model (e.g. model 10 and model 100). Exemplary computer aided design systems that are generally known to those skilled in the art include SOLIDWORKS, AUTODESK REVIT, AUTODESK INVENTOR, AUTOCAD, SKETCHUP, VECTORWORKS, MICROSTATION, ARCHICAD, and PROE. In certain embodiments, the computer aided design system is SOLIDWORKS.

To develop model 10, a computer aided design system is utilized to first create trachea portion 12. To create trachea portion 12, a circle with a predetermined diameter is first drawn on a top plane. In one or more embodiments, this circle diameter is 3.5 millimeters, or approximate thereto, in order to model the diameter of an infant's trachea. Next, the circle is extended to a predetermined length to create a 3D tube. In one or more embodiments, this length is 17.5 millimeters, or approximate thereto, in order to model the length of an infant's trachea. The thickness of the 3D tube may be set to any suitable thickness based on the planned method of fabricating the model.

Once trachea portion 12 is developed in the computer aided design system, first bifurcation 22 is developed. A pair of construction lines 40, 42 start at the bottom of trachea portion 12. Construction lines 40, 42 form a total bifurcation angle. In one or more embodiments, the total bifurcation angle of 80°, or approximate thereto. A perpendicular construction line 44, 46 is drawn perpendicular to each construction line 40, 42 to create the initial opening position of each daughter tube 28, 30. Perpendicular construction lines 44, 46 are made facing inward, and meet a point 52 in the center at which the two daughter tubes 28, 30 will split.

Figure 2:
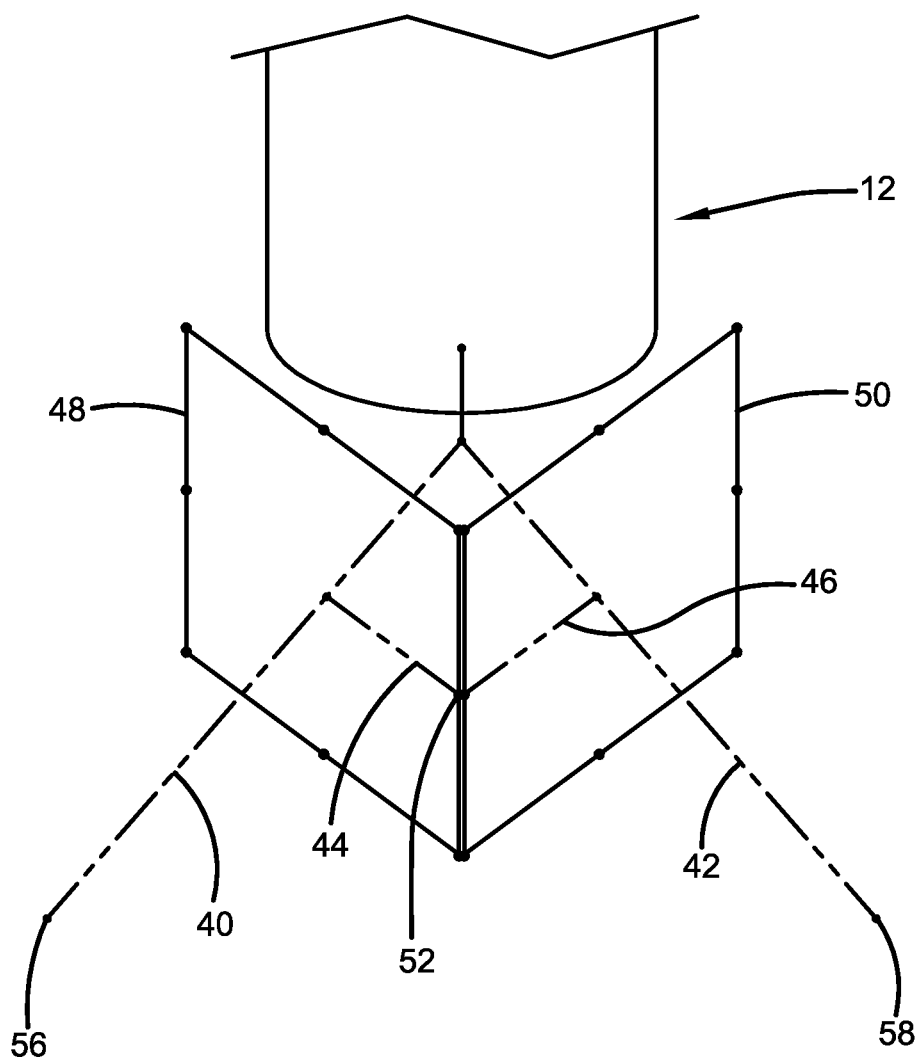
FIG. 2 is a schematic showing planes in which the first generation daughter tubes will be formed, for a symmetrical model.

Perpendicular construction lines 44, 46 are then dimensioned with the outer radius of the daughter tubes in that specific generation (e.g. FIG. 2 is generation z=1). Since the daughter tubes do not bifurcate until this point, construction lines 40, 42 are only dimensioned from this point forward. This means construction lines 40, 42 will be dimensioned with the airway length of the corresponding generation, but only from the points where perpendicular construction lines 44, 46 meet construction lines 40, 42.

After dimensioning all necessary lines, a plane 48, 50 is created on each of perpendicular construction lines 44, 46, where each plane 48, 50 is perpendicular to the respective construction lines 40, 42. At this point, the framework for bifurcation zone 22 is established. The two planes 48, 50 formed perpendicular to their respective initial construction lines 40, 42 are used to create the daughter tubes 28, 30.

Daughter tubes 28, 30 are developed by drawing a circle 54 of known diameter on each plane 48, 50. The diameter of circle 54 is known based on the relationship between trachea portion 12 diameter and the diameter of subsequent generations, $d_z = d_0 \times 2^{-z/3}$, discussed herein above. Each circle 54 passes through the splitting point where the bifurcation occurs. Then, using a 3D feature module in the computer aided design system, first branch 24, which may also be described as tube 24, is formed between this circle 54 and the bottom opening of the trachea portion 12. This 3D feature module is known as "lofting" in SOLIDWORKS software, and has an additional "thinning" method to create the structure as a hollow tube and to select the desired thickness. This 3D feature module step is repeated once more to create second branch 26, which may also be described as second tube 26, to complete the construction of bifurcation zone 22.

The development of daughter tubes 28, 30 may then be completed based on the above described relationship between airway diameter and airway length. Repeating here, it is generally known that the length of a subsequent generation human airway is three times, or approximate thereto, the diameter of the airway. This relationship may therefore be characterized as $L_z = 3d_z$. Thus, with the diameter of daughter tubes 28, 30 having been prescribed based on trachea portion 12 diameter, the length of daughter tubes 28, 30 is also prescribed based on $L_z = 3d_z$. In one or more embodiments, based on an initial trachea portion 12 diameter of 3.5 millimeters, each of first daughter tubes 28, 30 is 2.78 mm in diameter ($d_z = 3.5$ mm $\times 2^{-1/3} = 2.77795$ mm) and 8.33 mm long ($L_z = 3 \times 2.77795$ mm $= 8.33385$ mm).

As discussed elsewhere herein, daughter tubes 28, 30 also include a tapering from the first end to the second end. This tapering percentage may be fixed in order to determine the circular diameter at the second end. In one or more embodiments, the tapering is a 13.5% decrease between the diameter of the second end compared to the diameter of the first end. In other embodiments, the tapering is a decrease in a range of from 11% to 16%, in other embodiments, from 13% to 14%, between the diameter of the second end compared to the diameter of the first end. In one or more embodiments, based on an initial trachea portion 12 diameter of 3.5 millimeters, the diameter is 2.78 mm at the first end, so the diameter at the second end is prescribed to be 2.40 mm.

Based on the dimensioning of construction lines 40, 42, the second end 56, 58 of these lines 40, 42 may be prescribed. To continue the development of daughter tubes 28, 30, a perpendicular plane is made at the second end 56, 58 of each construction line 40, 42. Based on the prescribed tapering of daughter tubes 28, 30, a circle 60 of a prescribed diameter is drawn on each of the perpendicular planes. Then, the lofting feature of a computer aided design system may be used to connect circles 60 to those circles 54 created at bifurcation 22 where the opening of each daughter tube 28, 30 was made. This may also be described as daughter tubes 28, 30 being formed by elongating daughter tubes 28, 30 to accommodate the relationships.

Lastly, the wall thickness for the sidewall of daughter tubes 28, 30 may be selected for any suitable thickness. In one or more embodiments, the sidewall thickness is selected to retain transparency and fabrication feasibility. In one or more embodiments, the sidewall thickness is 500 μm, or approximate thereto.

The selection and application of a sidewall thickness completes the computer aided design system model for a model of generation $z=0-1$. Constructing additional generations using computer aided design system can be achieved by replicating the above described steps with respect to daughter tubes 28, 30. That is, a second generation of daughter tubes can be developed from a bifurcation from each of the first generation daughter tubes 28, 30, and so on, until a desired number of generations of daughter tubes. As provided elsewhere herein, subsequent generations of daughter tubes may be characterized based on utilizing the computer aided design systems to achieve a rotation of the daughter tubes within the 3D space. In one or more embodiments, generation $z=3$ of daughter tubes, rotates 90°, or approximate thereto, in the 3D space with respect to the plane of the generation $z=2$ of daughter tubes. In one or more embodiments, this rotation of 90°, or approximate thereto, continues for every subsequent generation of daughter tubes after $z=3$.

Figure 5:
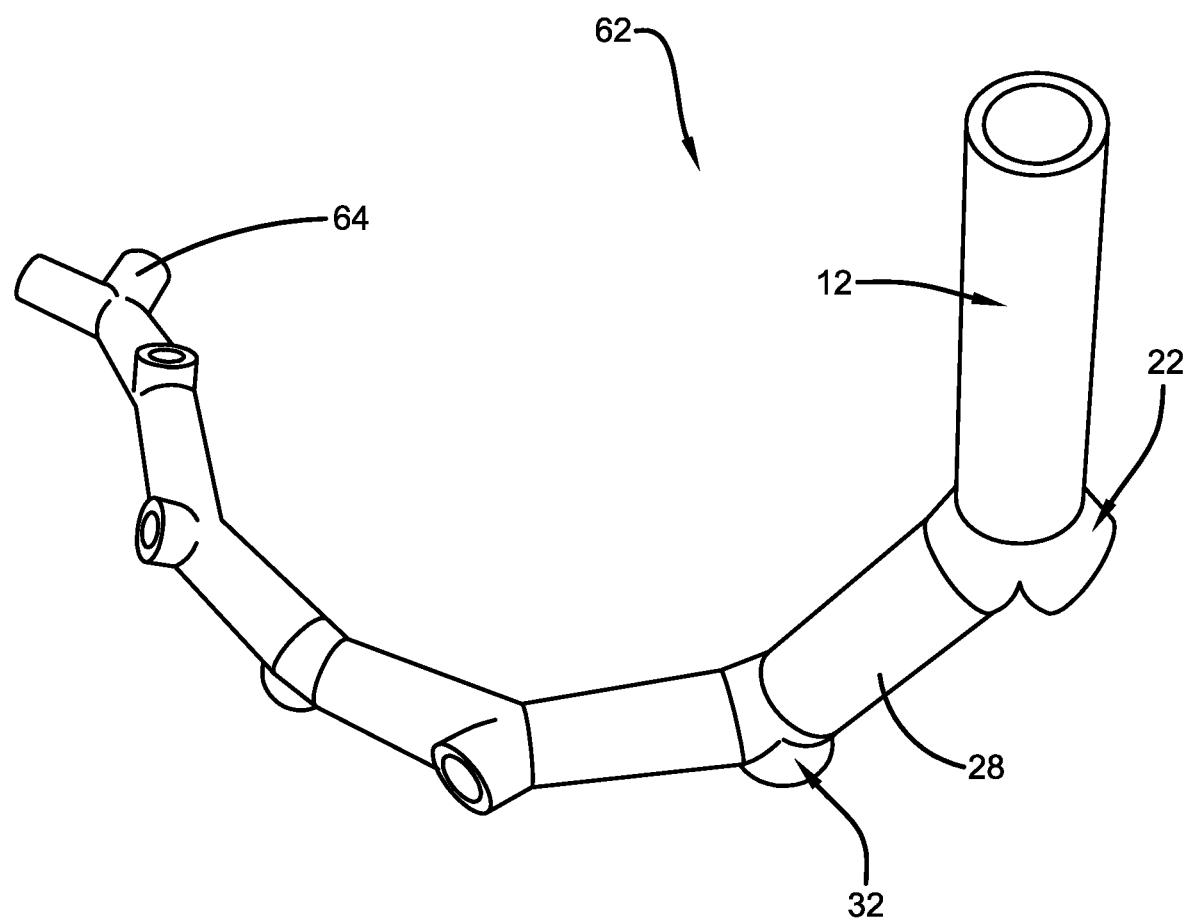
FIG. 5 is a schematic showing tubing of a seventh generation partial model, for a symmetrical model.
Figure 6:
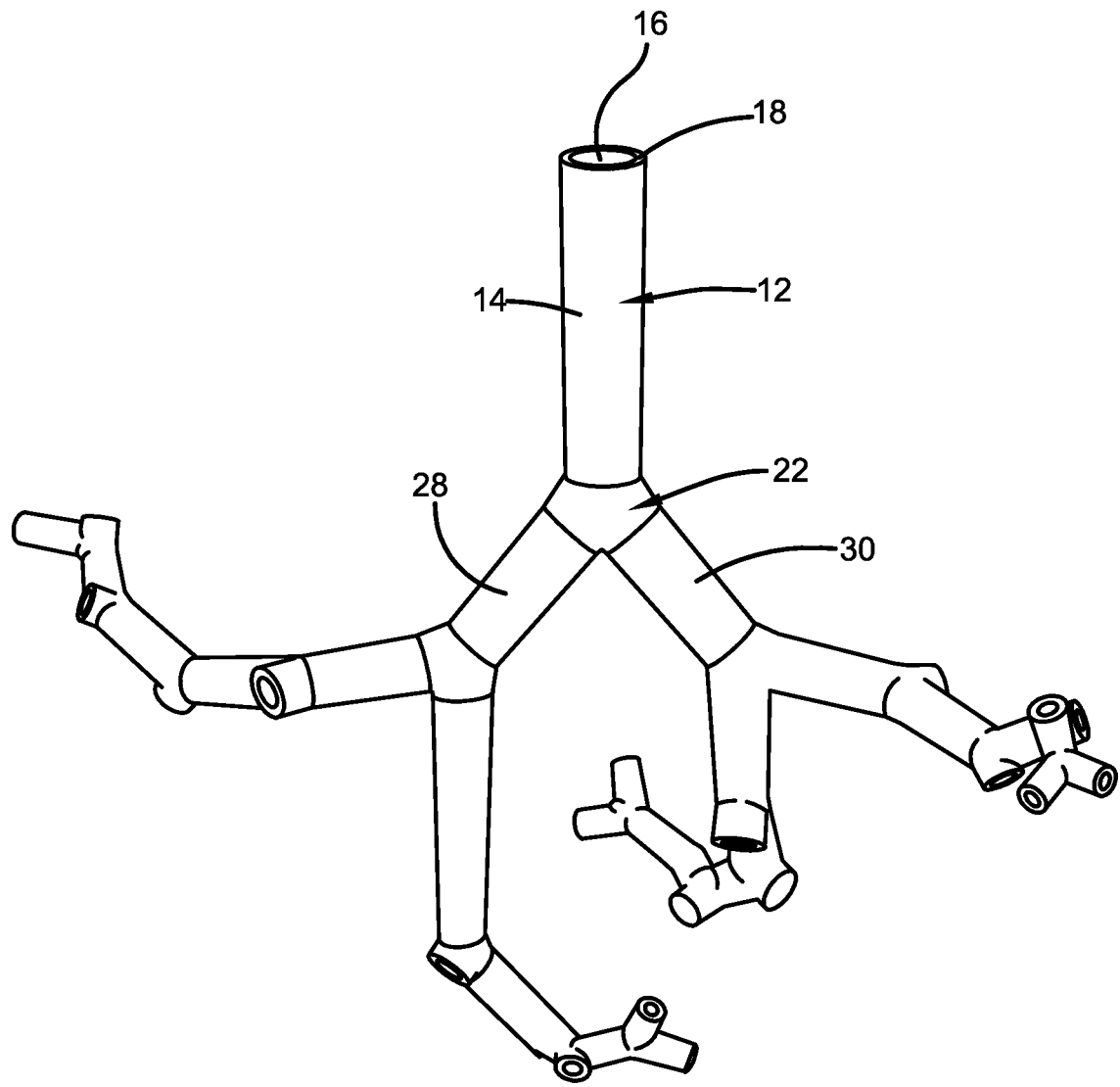
FIG. 6 is a schematic showing tubing of a seventh generation partial model, for a symmetrical model.

In one or more embodiments, symmetrical model 10 may be built using a strategy that includes first creating a single bifurcating airway unit 62 (FIG. 5) in a computer aided design system. Single bifurcating airway unit 62 includes trachea portion 12, bifurcation 22, and certain daughter tubes for a single airway up to an nth generation. FIG. 5 shows 7 generations. Single bifurcating airway unit 62 will allow for the replication process as described herein below.

Using a computer aided design system (e.g. SOLID-WORKS), trachea portion 12, bifurcation 22, and the daughter tubes shown in FIG. 5 are created in accordance with the above described method. Each generation prior to the 7th generation of single bifurcating airway unit 62 includes only one daughter tube. The 7th generation of single bifurcating airway unit 62 is formed with both daughter tubes 64. The 3rd generation and each generation thereafter are rotated 90° in the 3D space with respect to the plane of its preceding generation, as described above.

Trachea portion 12 and bifurcation 22 are then removed from single bifurcating airway unit 62, leaving an enclosed tube from the 1st generation through the 7th generation. This new resulting structure of the 1st generation through 7th generation tube is saved as a separate part in the computer aided design system.

Then, 1st generation daughter tube 28 and additional bifurcation 32 are removed from the 1st generation through 7th generation tube to form a 2nd generation through 7th generation tube. This 2nd generation through 7th generation tube is again saved as a separate part in the computer aided design system. This process repeats for each additional generation of daughter tube, with each removal of a daughter tube and corresponding bifurcation producing being saved as a separate part in the computer aided design system. Thus, each of the xth generation (i.e. 1, 2, 3, 4, 5, 6) through nth generation (e.g. 7 in FIG. 5) is saved as a separate part in the computer aided design system. The nth generation (e.g. 7 in FIG. 5) is also saved as a separate part in the computer aided design system. For the embodiment of FIG. 5, these seven parts and the part of trachea portion 12 and bifurcation 22 form eight different parts to be used for the assembly process of model 10.

To assemble model 10, the trachea portion 12 and bifurcation 22 is first provided in computer aided design system. As should be appreciated, this part includes two locations for the 1st generation through 7th generation tube to be positioned. The 1st generation through 7th generation part is thus positioned in the prescribed location of bifurcation 22 using the "mate" feature of the computer aided design system. Bifurcation 22 and the 1st generation through 7th generation part each include identical faces that can be matched using the "mate" feature of the computer aided design system, or other corresponding feature of the computer aided design system. The utilization of the "mate" feature of the computer aided design system, or other corresponding feature of the computer aided design system, may include the use of two mates to ensure the respective generation parts are oriented in the proper direction. The two mates involve using the physical faces of the connecting daughter tube to its opening, and the sketch of the opposite daughter tube to its corresponding opening.

After the two 1st generation through 7th generation parts are locked into place, there will be two locations for the 2nd generation through 7th generation tube to be positioned. The "mate" feature of the computer aided design system, or other corresponding feature of the computer aided design system, is utilized as described above to add the 2nd generation through 7th parts. After the two 2nd generation through 7th generation parts are locked into place, there will be four locations for the 3rd generation through 7th generation tube to be positioned. The "mate" feature of the computer aided design system, or other corresponding feature of the computer aided design system, is utilized as described above to add the 3rd generation through 7th parts. This process repeats through the nth generation of daughter tubes, such that all daughter tubes are formed as pairs of daughter tubes. There will be a total of $2^n$ daughter tubes in each generation, where n is the generation number.

Thus, the development of single bifurcating airway unit 62 within a computer aided design system, and the steps described above, allows single bifurcating airway unit 62 to serve as the building block to generate the complete model 10. Due to the symmetry of model 10, creating the model 10 utilizing the parts method described here provides a convenient approach to developing model 10.

To develop model 100, a computer aided design system is utilized to first create trachea portion 12, as described above. Once trachea portion 12 is developed in the computer aided design system, first bifurcation 102 is developed. A pair of construction lines 120, 122 start at the bottom of trachea portion 12. Construction lines 120, 122 form a total bifurcation angle. In one or more embodiments, the total bifurcation angle of 65°, or approximate thereto. In one or more embodiments, $\theta_1$ and $\theta_2$ may be characterized as described above.

A perpendicular construction line 124, 126 is drawn perpendicular to each construction line 120, 122 to create the initial opening position of each daughter tube 108, 110. Perpendicular construction lines 124, 126 are made facing inward, and meet a point 128 in the center at which the two daughter tubes 108, 110 will split.

Perpendicular construction lines 124, 126 are then dimensioned with the outer radius of the daughter tubes in that specific generation, where the radius may be sized based on previously known models of human lungs, such as the data of Raabe et al. (1976), discussed above and incorporated herein by reference. Since the daughter tubes do not bifurcate until this point, construction lines 120, 122 are only dimensioned from this point forward, where the length may be sized based on previously known models of human lungs, such as the data of Raabe et al. (1976), discussed above and incorporated herein by reference. This means construction lines 120, 122 will be dimensioned with the airway length of the corresponding generation, but only from the points where perpendicular construction lines 124, 126 meet construction lines 120, 122.

After dimensioning all necessary lines, a plane 130, 132 is created on each of perpendicular construction lines 124, 126, where each plane 130, 132 is perpendicular to the respective construction lines 120, 122. At this point, the framework for bifurcation zone 102 is established. The two planes 130 formed perpendicular to their respective initial construction lines 120, 122 are used to create the daughter tubes 108, 110.

Daughter tubes 108, 110 are first developed by drawing a circle 134, 136 of known diameter on each plane 130, 132. The diameter of circle 134, 136 may be sized based on previously known models of human lungs, such as the data of Raabe et al. (1976), discussed above and incorporated herein by reference.

Each circle 134, 136 passes through the splitting point where the bifurcation occurs. Then, using a 3D feature module in the computer aided design system, first branch 104, which may also be described as tube 104, is formed between this circle 134 and the bottom opening of the trachea portion 12. This 3D feature module is known as "lofting" in SOLIDWORKS software, and has an additional "thinning" method to create the structure as a hollow tube and to select the desired thickness. This 3D feature module step is repeated once more to create second branch 106, which may also be described as second tube 106, to complete the construction of bifurcation zone 102.

The development of daughter tubes 108, 110 may then be completed based on previously known models of human lungs, such as the data of Raabe et al. (1976), discussed above and incorporated herein by reference. As discussed elsewhere herein, daughter tubes 108, 110 may include a tapering from the first end to the second end. This tapering percentage may be fixed. In one or more embodiments, the tapering is a 13.5% decrease between the diameter of the second end compared to the diameter of the first end.

Based on the dimensioning of construction lines 120, 122, the second end 138, 140 of lines 120, 122 is prescribed. To continue the development of daughter tubes 108, 110, a perpendicular plane 142 is made at the second end 138, 140 of each construction line 120, 122. Based on the prescribed tapering of daughter tubes 108, 110, a circle 144 of a prescribed diameter is drawn on each of the perpendicular planes 142. Then, the lofting feature of a computer aided design system may be used to connect circles 144 to those circles 136 created at bifurcation 102 where the opening of each daughter tube 108, 110 was made. This may also be described as daughter tubes 108, 110 being formed by elongating daughter tubes 108, 110 to accommodate the dimensioning.

Lastly, the wall thickness for the sidewall of daughter tubes 108, 110 may be selected for any suitable thickness. In one or more embodiments, the sidewall thickness is selected to retain transparency and fabrication feasibility. In one or more embodiments, the sidewall thickness is 500 µm, or approximate thereto.

The selection and application of a sidewall thickness completes the computer aided design system model for a model of generation z=0-1. Constructing additional generations using computer aided design system can be achieved by replicating the above described steps with respect to daughter tubes 108, 110. That is, a second generation of daughter tubes can be developed from a bifurcation from each of the first generation daughter tubes 108, 110, and so on, until a desired number of generations of daughter tubes. The subsequent generations may also be based on previously known models of human lungs, such as the data of Raabe et al. (1976), discussed above and incorporated herein by reference. As provided elsewhere herein, subsequent generations of daughter tubes may be characterized based on utilizing the computer aided design systems to achieve a rotation of the daughter tubes within the 3D space. In one or more embodiments, generation z=3 of daughter tubes, rotates 90°, or approximate thereto, in the 3D space with respect to the plane of the generation z=2 of daughter tubes. In one or more embodiments, this rotation of 90°, or approximate thereto, continues for every subsequent generation of daughter tubes after z=3.

Since model 100 lacks symmetry, model 100 cannot be made by using the assembly process described above with respect to model 10. To create the asymmetric model 100, each bifurcation and corresponding daughter tubes are separately constructed for every generation.

In one or more embodiments, after completing the computational designs for a model (e.g. model 10 and model 100) within a computer aided design system, the model may be fabricated based on the computational design. This fabrication may provide a physical model in order to study surfactant distribution in the airways. The process of providing a computational design of a model to a fabrication apparatus is generally known to those skilled in the relevant art.

In one or more embodiments, a model is fabricated using an additive manufacturing technique, also known as 3D printing. As generally known in the art, this may include the computer aided design system or other related software mathematically slicing the computer file, i.e. computer model, into a plurality of thin layers, with the additive manufacturing apparatus using the sliced computer model to build the object model layer by layer. This forms a sliced computer file. The number of sliced layers may be suitably large based on the desired additive manufacturing process, as generally known to those skilled in the art. This layer by layer development may start with the bottom layer, on an elevator that is lowered slightly after solidification of each layer. Each layer may be formed at any suitable thickness. In one or more embodiments, each layer is 200 µm thick, or approximate thereto. In one or more embodiments, an additive manufacturing technique has a resolution of 50 µm, or approximate thereto. Other generally known techniques may include forming and copying the 3D object without forming layers thereof.

In one or more embodiments, an additive manufacturing method is stereolithography. In one or more embodiments, an additive manufacturing apparatus is a stereolithographic system. As generally known in the art, stereolithography forms the layers using photopolymerization, a process by which light causes chains of molecules to link. As generally known, a photopolymerizable polymer is extruded through a nozzle onto a surface in the form of layers and each layer is cured using radiation, such as UV light. An exemplary stereolithographic system is marketed under the trade designation "VIPER SLA".

In one or more embodiments, a model is fabricated from a transparent material. In one or more embodiments, a model is fabricated from a resin. In one or more embodiments, a model is fabricated from a photosensitive resin. An exemplary photosensitive resin is an ABS (acrylonitrile butadiene styrene)-like photopolymer available under the trade designation "SOMOS WATERSHED XC 11122". Another exemplary photosensitive resin is a photopolymer available under the trade designation "SOMOS WATERCLEAR ULTRA 10122". In one or more embodiments, a photosensitive resin may be characterized as water resistant. In one or more embodiments, a photosensitive resin may be characterized as substantially colorless and transparent after full cure.

In one or more embodiments, SOMOS WATERCLEAR ULTRA 10122 includes between 45-70 wt % of epoxies, 10-25 wt % of acrylates, 5-15 wt % of oxetane, 5-15 wt % of polyol, 5-15 wt % of photoinitiators, and 0-10 wt % of additives. In one or more embodiments, SOMOS WATERSHED XC 11122 includes between 45-70 wt % of epoxies, 5-20 wt % of acrylate, 10-25 wt % of oxetane, 5-15 wt % of photoinitiators, and 0-10 wt % of additives.

The use of a transparent model allows visualizing the interior of the airways. This visualization of the interior of airway tubes helps analyze surfactant distribution in airways. In one or more embodiments, the term "transparent" may therefore be characterized as the ability to optically view surfactant flow and distribution within the model. The ability to optically view surfactant flow and distribution within the model allows for the study of the surfactant distribution under various delivery conditions.

In one or more embodiments, the trachea portion 12 may be made as a rigid, inflexible object in order to match the cartilaginous properties of a human trachea. In one or more embodiments, first generation daughter tubes may be made as rigid, inflexible objects. In one or more embodiments, first generation daughter tubes may be made as flexible objects. In one or more embodiments, second generation daughter tubes may be made as rigid, inflexible objects. In one or more embodiments, second generation daughter tubes may be made as flexible objects. In one or more embodiments, third generation daughter tubes and subsequent generation daughter tubes may be made as flexible objects.

As provided in the Example below, model 10 and model 100 may be utilized to develop delivery strategies for uniform distribution of therapeutic fluids in human lungs. This may be based on analyzing model 10 or model 100 for the effects of one or more of geometry of airways, fluid properties, and flow characteristics on liquid plug splitting. This may also be based on one or more of the orientation of bifurcating airways, inertia, gravity, and surface tension.

Figure 11:
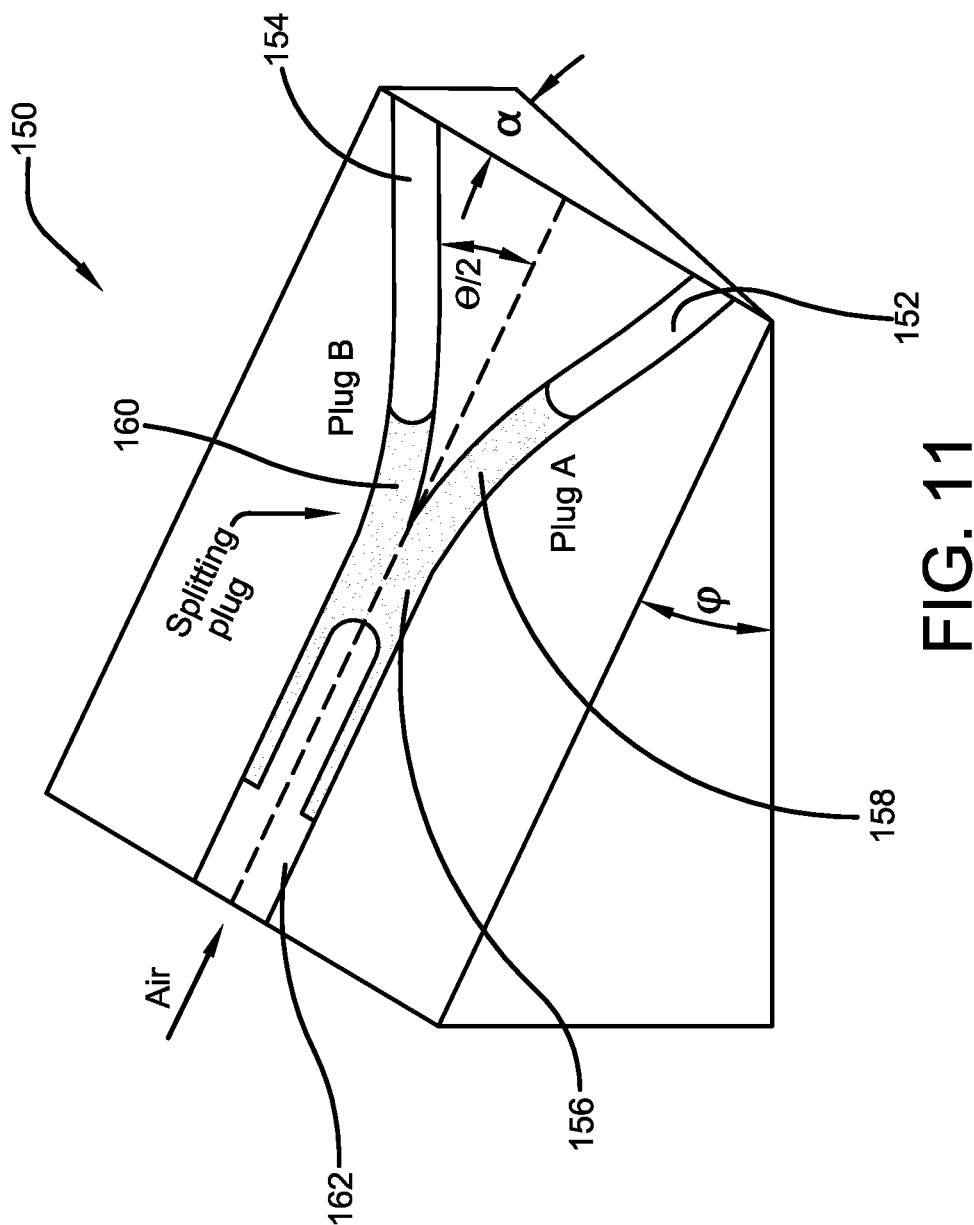
FIG. 11 is a schematic showing a testing apparatus for the flow between a pair of daughter tubes, showing the roll angle ($\alpha$) and the pitch angle ($\varphi$) and a liquid plug splitting at the bifurcation.

With reference to FIG. 11, one or more embodiments of the present invention provide a testing apparatus 150 for analyzing the flow between a pair of daughter tubes 152, 154. Testing apparatus 150 includes fluid 156 that may split at a bifurcation 158. This may form a liquid plug A 158 in lower daughter tube 152 and a liquid plug B 160 in upper daughter tube 154.

When a plug of fluid 156 reaches bifurcation 158, it divides at some ratio between the two daughter tubes 152, 154. This may be characterized as a split ratio, R, which may be provided as the ratio of the length of plug 160 in the upper daughter tube 154 to the length of plug 158 in the lower daughter tube 152, i.e. the gravitationally favored tube, after splitting is complete. This may be given as $R=L_B/L_A$.

The orientation of a model, and any particular airway unit thereof, in the gravitational field influences the flow characteristics, thereby determining the split ratio. The flow characteristics may be given by characterized by a roll angle ($\alpha$), a pitch angle ($\varphi$), and gravitational acceleration (g). As shown in FIG. 11, a represents relative gravitational orientation of daughter tubes 152, 154. When $\alpha>0°$, one daughter tube is gravitationally favored. In FIG. 11, tube 152 is gravitationally favored.

As shown in FIG. 11, $\varphi$ specifies the component of gravity acting along axial direction of the parent tube 162. When $\varphi>0°$, gravity acts along the direction of motion of plug 156 in parent tube 162. At $\alpha=0°$ and $\varphi=0°$, the testing apparatus 150, which may also be referred to as an airway unit 150, is horizontal. An accelerometer (not shown) associated with testing apparatus 150 allows for precise adjustments of $\alpha$ and $\varphi$.

When using testing apparatus 150 for analysis, the orientation of testing apparatus 150 may be adjusted for any suitable roll angle ($\alpha$) and pitch angle ($\varphi$). In one or more embodiments, roll angle ($\alpha$) may be 0°, in other embodiments, 30°, in other embodiments, 60°, and in other embodiments 90°. In one or more embodiments, roll angle ($\alpha$) may be less than 30°, in other embodiments, less than 60°, and in other embodiments less than 90°. In one or more embodiments, pitch angle ($\varphi$) may be 0°, in other embodiments, 15°, and in other embodiments, 30°. In one or more embodiments, pitch angle ($\varphi$) may be less than 15°, and in other embodiments, less than 30°.

As provided in the Example below, one or more embodiments show feasibility of delivering a surfactant solution into a model, and also human lungs, using smaller orientations than what is currently used clinically. Significantly, the results show that producing a fairly even split ratio in generation z=1-2 may lead to uniform surfactant distribution in subsequent airways because surface forces become more and more dominant with the reduction in airway size, reducing the effect of orientation of airways in the gravitational field.

In one or more embodiments, a fabricated model (e.g. model 10 and model 100) may be utilized for mimicking disease conditions. For example, cystic fibrosis is a progressive, genetic disease that causes persistent lung infections and limits the ability to breathe over time. Bacterial infection of the lung airways results in the failure of the lung's defense against inhaled pathogens. The inaccessibility the lung airways of a human patient does not allow for effective evaluation of the efficacy of administered medications. A fabricated model may be utilized to generate the infection conditions within the fabricated model, to mimic the bacterial infection of cystic fibrosis. A fabricated model having the infection conditions could then be utilized to evaluate treatments administered to the fabricated model.

In one or more embodiments, a fabricated model (e.g. model 10 and model 100) may be utilized for evaluating surfactant treatment. Premature babies generally lack naturally-produced surfactant in their lungs; the surfactant is vital to respiration. To assist premature babies with breathing exogenous surfactant is administered through the trachea to distribute to the lungs. The non-response rate to this exogenous administration is around 30%. A fabricated model, particularly a model sized to model a premature baby's lungs, may be utilized to directly observe administered surfactant. An exemplary surfactant is available under the trade name Infasurf from ONY, Inc. Infasurf is an intratracheal suspension derived from the natural surfactant in calf lungs.

In one or more embodiments, a radiofrequency oxygen plasma for 1 min to render the interior surface of the airways hydrophilic. In one or more embodiments, one end of a silicon tubing may be connected to the first end of a trachea portion of a fabricated model with the second end of the silicon tubing being attached to a plastic syringe mounted on a syringe pump, for injecting a therapeutic fluid. In one or more embodiments, a therapeutic fluid may be first applied to a fabricated model, with air subsequently injected to flow the therapeutic fluid fully through the fabricated model.

This analysis will then enable the development of improved strategies for treating premature babies. This may include an exogenous surfactant administration that is more delivered more uniformly, and therefore more efficiently.

In light of the foregoing, it should be appreciated that the present invention advances the art by providing improved modeling of a lung airway tree. While particular embodiments of the invention have been disclosed in detail herein, it should be appreciated that the invention is not limited thereto or thereby inasmuch as variations on the invention herein will be readily appreciated by those of ordinary skill in the art. The scope of the invention shall be appreciated from the claims that follow.

EXAMPLES

Example

A clinical surfactant, Infasurf (ONY, Inc.) was used to study the flow through a model. The surfactant was at a 35 mg/mL phospholipids concentration, and is commonly used for treating preterm babies. Dynamic viscosity of Infasurf fluid was measured using a rheometer and plotted against shear rate. Due to the non-Newtonian nature of Infasurf, this plot was used to identify the viscosity at the experimental flow rates that were used to determine the shear rate from known diameters in each generation. The surface tension was not measured, but was taken from a previous study as $\gamma_{Infasurf}=25$ dynes/cm. The density of Infasurf was measured as $\rho_{Infasurf}=0.980$ g/cm$^3$.

The experimental setup and plug splitting experiments were similar to as described above. Symmetric, multi-generation 3D airway tree models were used. The airway models were placed on a 0.5-inch thick plexiglass platform that was held fixed using clamps on a gyroscopic mount. An accelerometer was mounted on the plexiglass platform to allow precise adjustments of the orientation of airway models with respect to the gravitational field using a roll angle ($\alpha$) and a pitch angle ($\varphi$). Experiments were done at different combinations of $\alpha=0°$, 30°, 60°, and 90° and $\varphi=0°$ and 15°. Prior to plug splitting experiments, each airway model was exposed to radiofrequency oxygen plasma (Harrick Plasma) for 1 min to render the interior surface of the airways hydrophilic. The airway model was fixed on the test platform. Next, 75 µl of the working fluid was loaded into a pipette tip, which was placed inside the tracheal tube of the airway model. The fluid was injected into the tracheal tube using a positive displacement pipette to form a liquid plug. Silicon tubing (Tygon) was connected to the tracheal tube of the model from one end and to a plastic syringe (NormJect) mounted on a syringe pump (Chemyx Inc.) from the other end. Pre-defined airflow rates were used to propagate plugs within the airway tree models to accommodate pre-defined Capillary numbers (C$\alpha$) that would allow an imaging system to capture propagating plugs. With the Infasurf solution, airflow rates of 12.095, 18.186, and 28.285 ml/min were used.

An imaging protocol was utilized to record each experiment as a movie at a rate of 25 fps using a SLR camera (Nikon D3100) equipped with a macro lens (Tamron). Videos were converted to individual frames. The length of the plug in the parent tube right before splitting and the length of each of resulting plugs in the daughter tubes right after splitting was measured in ImageJ (NIH). A split ratio was defined as the ratio of the lengths of the two daughter plugs in the upper and lower daughter tubes, i.e., as $R=L_B/L_A$. To accurately measure the plugs in generations z=0-1 and z=1-2 of the airway tree models, the volume of the two daughter plugs were estimated and the split ratio was defined as $R=V_B/V_A$, defined below. Experiments at any particular orientation of the airway tree models had at least three replicates to obtain an average R value. Statistics were done using a t-test. Statistical significance was defined at p values less than 0.05.

A split ratio at bifurcation z=0-1 was analyzed. The image analysis of plug splitting was very important to quantify the split ratio at each generation and enable quantitative conclusions about surfactant distribution under various experimental conditions such as orientation of the airway tree and flow rate. The image analysis began with the plug formed in the tracheal tube of the model. At this point, the plug was stationary and air had not been pumped to drive it into the model. The next significant image was after the plug splits at the first bifurcation, i.e., z=0-1. In this case with a roll angle of $\alpha=30°$ and a pitch angle of $\varphi=0°$, it could be seen that more surfactant solution flowed into one side of the airway tree. Assuming that an infant is placed on its back and oriented according to these roll and pitch angles, more surfactant would flow into the infant's left lung. However, to quantify the split ratio is not as simple as taking the ratio of the lengths of each plug because the daughter plug spans from the primary to secondary bronchi in the left lung but the daughter plug in the right lung only partially occupies the primary bronchi. To resolve this issue, it was estimated for the volumes of the plugs and defining a split ratio based on volume ratios, i.e., $R=V_B/V_A$. For all the measurements taken, "A" refers to the left lung while "B" refers to the right lung, and "1" indicates the left tube while "2" indicates the right tube in each bifurcation. Note that left and right lungs are defined considering that an infant is placed on its back during SRT. The measurements for generation z=0-1 were determined. First, $L_{A1}$ was measured from the beginning of z=1 where the plug split at the initial bifurcation, and extended down to the end of the first generation where the next bifurcation, z=1-2, begins. The next measurement occurred in the bifurcation zone of z=1-2. This zone created an isosceles triangle with the base being equal to the diameter of the z=1 tube. Since the area of a triangle is A=1⁄2*b*h, the height of the triangle, $L_{A\Delta}$, can be measured and then divided in half to accurately represent the area covered. These lengths were then used to calculate the volumes of the surfactant solution using volume formula for a cylinder, i.e., $V_{A1}=(L_{A1}+L_{A\Delta}/2)*(\pi*R_{A12})$, where $R_{A1}$ represents the radius of the left primary bronchi denoted by the subscript A1. Next, the lengths of the two plugs that span into the second generation (z=2), $L_{A11}$ and $L_{A12}$, were measured, starting from the beginning of the tube and extending it to the end of the plug. Since these two plugs were in the same airway generation of the same radius, their total volume becomes $V_{A11}+V_{A12}=(L_{A11}+L_{A12})*(\pi*R_{A112})$. These measurements were used to obtain the final volume, $V_A$, of plug A by adding up all the volumes in the left lung as $V_A=(V_{A11}+V_{A12}+V_{A1})$. Then for the right lung, $L_B$ was measured and converted to a volume $V_B=L_B*(\pi*R_{B2})$. Finally, the split ratio for z=0-1 was obtained where $R=V_B/V_A$.

A split ratio at bifurcation z=1-2 was analyzed. Since airways in generations z=0, 1, and 2 were in the same plane, the imaging system could conveniently capture the split ratio at both bifurcations z=0-1 and z=1-2. But starting from generation z=3, airways rotated 90° with respect to their parent airway. This introduced major difficulties with imaging of splitting plugs and its quantification. As seen for the plug splitting in z=1-2 for the left lung of the airway tree, the plug did not evenly split between the two daughter tubes of the z=2 generation. More surfactant solution flowed into the left daughter tube. Because the volume of the surfactant solution entered the z=2 airway was larger than the volume of the airway tube, the surfactant solution further flowed into the next generation airway tubes (z=3). This airway tube had a 90° rotation with respect to the z=2 airway, making it difficult to accurately capture the process with the existing imaging system using a single camera. To overcome this limitation and determine the split ratio in this generation, a total volume, $V_A$, in the left daughter tube of z=2 was used. First, the length of $L_{A12}$ was measured and converted it to a volume, $V_{A12}=L_{A12}*(\pi*R_{A122})$. Then $V_{A11}$ was found by subtracting $V_{A12}$ from the total volume of the plug in the left lung, i.e., $V_{A11}=V_A-V_{12}$. The split ratio for the z=1-2 bifurcation in the left lung was determined as $R=V_{A12}/V_{A11}$.

The split ratio was also measured at the z=1-2 bifurcation of the right lung. Since this side was leaning away from gravity for our experiments, plugs in the airway tubes were generally smaller and did not flow into the airways of the subsequent generation. This simplified finding the split ratio by measuring the length of both plugs, $L_{B21}$ and $L_{B22}$, and converting them to volumes. The split ratio for the z=1-2 bifurcation in the right lung was then determined as $R=V_{B22}/V_{B21}$. However, if the plugs flow into the next generation, the same procedure defined above for the left lung could be used to find the split ratio.

The split ratio at any specific orientation of a single bifurcating airway unit in the gravitational field was determined by some combination of viscous, surface tension, inertia, and gravitational forces. To demonstrate the effect of orientation on the distribution of instilled surfactants in the lung, symmetric, multi-generation, 3D airway tree models were used to gain a quantitative understanding of this process.

To investigate splitting of liquid plugs between the two daughter tubes of multi-generation airway models, each airway tree was oriented at three different role angles of $\alpha=30°$, 60°, and 90°. The rationale for this selection of this range for the roll angle is based on SRT where babies may be oriented anywhere from lying on their back to completely on one side. Initially, the pitch angle was kept at $\varphi=0°$. The roll and pitch angles were defined for the z=0-1 unit of airway tree models. Due to the capturing speed limitations of our imaging system, small range of Ca's could be covered that were on a similar order of magnitude. Therefore, plug splitting data at each specific orientation that only showed small variations with changing the Ca were averaged and represented as a function of an average Ca. At an average Ca of about 0.034, the increase in the roll angle from $\alpha=0°$ to $\alpha=30°$ caused more than 75% of the plug solution to drain into the lower daughter tube and resulted in a split ratio of 0.31±0.11. Further increase in $\alpha$ to 60° and 90° decreased R to 0.08±0.04 and 0.07±0.03, respectively. This was a total reduction of about 95% in the split ratio from R≈1 at a horizontal orientation) ($\alpha=\varphi=0°$). This result clearly showed that the roll angle substantially affected surfactant distribution between the left and right lungs at z=0-1. Rolling the airway unit farther away from a horizontal orientation simply increased the asymmetry of splitting of the liquid plug between the two daughter tubes. It was expected that a significant increase in Ca, e.g., by an order of magnitude, would somewhat counteract this gravity-driven drainage into the lower daughter tube, but the effect of orientation will be dominant.

In the z=1-2 bifurcation, the plug splitting results between the left and right lung were quite different. For the left lung, at an average Ca of 0.027, the increase in the roll angle from $\alpha=0°$ to $\alpha=30°$ caused more than 70% of the plug solution to drain into the lower left daughter tube and resulted in a split ratio of 0.40±0.07. Increasing a to 60° and 90° decreased R to 0.24±0.05 and 0.18±0.06. This is consistent with the effect of roll angle for the z=0-1 bifurcation and the amount of the surfactant solution that drained into the lower left daughter tube ranges from 70-85% in z=1-2 compared to 75-95% in the lower daughter tube in z=0-1. This difference was likely due to the initial orientation of the daughter tubes, since in generation z=0-1 the upper daughter tube was pointed further away from gravity, while in generation z=1-2 in the left lung the upper/right daughter tube was almost horizontal. This allowed more surfactant to follow the path of least resistance into the lower daughter tube of the z=0-1 bifurcation. The smaller diameter of airway tubes in z=1-2 also reduced the effect of gravity.

In the z=1-2 bifurcation of the right lung, at an average Ca of about 0.027, the increase in the roll angle from $\alpha=0°$ to $\alpha=30°$ had little effect and resulted in a split ratio of 0.95±0.11. An increase in a to 60° and 90° only marginally changed R to 0.77±0.08 and 0.83±0.05. Therefore, regardless of the value of the roll angle, the plug split nearly evenly between the two daughter tubes. Due to the orientation of the right daughter tube of the z=1 generation farther away from a horizontal plane by increasing the roll angle, the volume of the daughter tube that flowed into this airway is very small. As a result, a small volume of the surfactant solution flowed into the right lung. The small volume of the surfactant solution in the right lung often resulted in the plugs rupturing before reaching the end of the 5th generation airways. From a practical standpoint, this meant that the surfactant solution may not sufficiently reach the alveoli during SRT. However, because most of the surfactant solution flowed into the left lung, the alveoli of the left lung would be coated with the surfactant solution. Therefore, this suggested that orienting the infant once to the left and then to the right and performing surfactant instillation twice may produce the desired therapeutic effect.

Collectively, this study suggested that the splitting of liquid plugs at bifurcations was dependent on the orientation of the airway model and a significant quantity of the solution drained into the gravitationally favored daughter tubes. The importance of orientation was shown for the first two airway generations to demonstrate how the initial split ratio at the z=0-1 bifurcation greatly affected surfactant distribution between daughter tubes of the z=2 generation airways for both the left and right lung. The significant effect that each roll angle had on the first two generations could be viewed in the p values resulting from the statistical analysis of the split ratio data. In addition, comparing the split ratio results for the airway tree model for generation z=0-1 with corresponding single bifurcation models showed close agreement.

To elucidate the effect of positioning the airway models away from a horizontal plane through the pitch angle on the splitting of liquid plugs, each airway tree model were fixed at a roll angle of $\alpha=0°$ or $\alpha=30°$ then adjusted the pitch angle to $\varphi=15°$. For the $z=0$-$1$ bifurcation at $\alpha=0°$ and with an average Ca of about 0.034, increasing the pitch angle to $\varphi=15°$ did not have any effect on plug splitting and a symmetric splitting was maintained, i.e., $R=1.02\pm0.06$. However, when $\alpha=30°$ and the pitch angle was set to 15°, the splitting becomes highly asymmetrical and a split ratio of $R=0.11\pm0.06$ resulted. This was a reduction of 0.2 in the split ratio at the same roll angle, but without pitching. This drastic decrease in the split ratio was because pitching the model after rolling it made the lower daughter tube more gravitationally favored, and a larger volume of the surfactant solution drained into it. Another conclusion was that the roll angle has a greater effect than the pitch angle on surfactant distribution between daughter tubes emerging from the $z=0$-$1$ bifurcation.

For the $z=1$-$2$ bifurcation of the left lung, introducing a pitch angle had a greater effect on the split ratio than in $z=0$-$1$. At an average Ca of about 0.027, when the pitch angle was increased to $\varphi=15°$ but keeping the roll angle zero increased the split ratio from unity to $R=1.64\pm0.13$. Introducing a pitch angle made the daughter tube on the right-hand side of the bifurcation zone of $z=1$-$2$ more gravitationally favored and surfactant flowed more into it. Increasing the roll angle from 0° to 30° while keeping $\varphi=15°$ opposed the effect and made the daughter tube to the left of the bifurcation zone more gravitationally favored, resulting in a drop in the split ratio to $R=0.57\pm0.23$. This was still 0.17 units larger than the split ratio without pitching the model. Despite a small effect of the pitch angle on splitting at the $z=0$-$1$ bifurcation, it had a major effect on the distribution of surfactant between the two lobes of the left lung. Thus, these data suggested that the pitch angle can be used to more direct surfactant into a specific lobe of the left lung. The significance of the pitch angle effect on plug splitting was shown in the statistical analysis of p values.

For the $z=1$-$2$ bifurcation in the right lung, at an average Ca of about 0.027, increasing the pitch angle by 15° and keeping the roll angle at zero degrees made a minor change in the split ratio to $R=1.04\pm0.03$. When the roll angle was also increased to 30°, the split ratio dropped to $0.82\pm0.11$, which was only 0.13 units smaller than that without pitching the unit. Since the 3D model was symmetric, it was expected that only pitching 15° to have had the same effect on the right lung as it did for the left lung. However, this was not the case and was likely due to a 15° offset, which was introduced to prevent the lower airway generations from overlapping. When positioned horizontally on the platform, the left lung in the model was offset 15° downward from a horizontal position, and the right lung was offset 15° upward from a horizontal position. This offset likely created a more pronounced effect on the split ratio in the left lung, while counteracting the effect of pitch angle in the right lung.

The preliminary data suggested it is potentially feasible to deliver surfactant solution into lungs using smaller orientations than what is currently used clinically. Significantly, the results showed that producing a fairly even split ratio in generation $z=1$-$2$ may lead to uniform surfactant distribution in subsequent airways because surface forces become more and more dominant with the reduction in airway size, reducing the effect of orientation of airways in the gravitational field.

Various modifications and alterations that do not depart from the scope and spirit of this invention will become apparent to those skilled in the art. This invention is not to be duly limited to the illustrative embodiments set forth herein.

What is claimed is:

1. A method of producing a model of a human lung, the method comprising steps of
  preparing a computer file within a computer aided design system utilizing steps of
    forming a trachea portion having a first end and a second end,
    forming a first bifurcation zone at the second end of the trachea portion, the first bifurcation zone having a first branch and a second branch,
      wherein the step of forming a first bifurcation zone includes steps of
      extending two construction lines from the second end of the trachea portion, where the two construction lines form a total bifurcation angle,
      extending a perpendicular construction line from a point on each of the two construction lines, each of the perpendicular construction lines extending inward until meeting at a point,
      dimensioning one of the perpendicular construction lines based on a predetermined value for a radius of the first generation bronchi tube to form a dimensioned perpendicular construction line, and
      forming a plane along the dimensioned perpendicular construction line,
    extending a first generation bronchi tube from the first branch of the first bifurcation zone, the first generation bronchi tube having a distal end,
      wherein the step of extending a first generation bronchi tube includes steps of
      forming a first circle having a predetermined diameter along the plane along the dimensioned perpendicular construction line,
      dimensioning one of the construction lines, starting from the point on the construction line and based on a predetermined value for a length of the first generation bronchi tube, to thereby form a dimensioned construction line having a distal point,
      forming a plane along the distal point of dimensioned construction line, and
      forming a second circle having a predetermined diameter along the plane along the distal point of dimensioned construction line,
    forming a subsequent bifurcation zone at the distal end of the first generation bronchi tube, which may be referred to as a prior generation bronchi tube, the subsequent bifurcation zone having a first branch and a second branch,
    extending a subsequent generation bronchi tube from the first branch of the subsequent bifurcation zone, which may be referred to as a prior bifurcation zone, the subsequent generation bronchi tube having a distal end,
    repeating the steps of
      forming a subsequent bifurcation zone at the distal end of the prior generation bronchi tube, the subsequent bifurcation zone having a first branch and a second branch, and
      extending a subsequent generation bronchi tube from the first branch of the prior bifurcation zone,
    until a predetermined number of generations of bronchi tubes have been formed,
  wherein the computer file is adaptable with an additive manufacturing apparatus, providing the computer file to the additive manufacturing apparatus, fabricating, with the additive manufacturing apparatus, a 3D object based on the computer file.

2. The method of claim 1, wherein at least a third generation bronchi tube is formed, wherein the third generation bronchi tube is rotated 90° in the 3D space with respect to the prior generation bronchi tube.

3. The method of claim 1, wherein the predetermined number of bronchi tubes is greater than three, wherein the third generation bronchi tube and each subsequent generation bronchi tube is rotated 90° in the 3D space with respect to the prior generation bronchi tube.

4. The method of claim 1, wherein the predetermined number of generations of bronchi tubes is defined as n, wherein, after the predetermined number of generations of bronchi tubes have been formed, the step of preparing a computer file further comprises steps of separating the trachea portion and the first bifurcation zone from the first generation bronchi tube to form a trachea portion and first bifurcation zone part and a first generation bronchi tube through n generation bronchi tube part, saving the trachea portion and the first bifurcation zone as a part within computer aided design system, saving the first generation bronchi tube through n generation bronchi tube part as a part within computer aided design system, separating the first generation bronchi tube and the subsequent bifurcation zone from the subsequent generation bronchi tube to form a subsequent generation bronchi tube through n generation bronchi tube part, saving the subsequent generation bronchi tube through n generation bronchi tube part as a part within computer aided design system, adding the saved first generation bronchi tube through n generation bronchi tube part to the second branch of the first bifurcation zone, and adding the saved subsequent generation bronchi tube through n generation bronchi tube part to the second branch of the subsequent bifurcation zone.

5. The method of claim 1, wherein the 3D object is transparent.

6. The method of claim 1, wherein the additive manufacturing apparatus is a stereolithographic system.

7. The method of claim 1, wherein the 3D object is made from an (acrylonitrile butadiene styrene)-like photopolymer.

8. The method of claim 1, wherein the computer aided design system is SOLIDWORKS.

9. The method of claim 1, wherein the total bifurcation angle is 80°.

10. The method of claim 1, further comprising a step of injecting a surfactant into the 3D object to thereafter analyze the flow of the surfactant through the 3D object.

11. A method of producing a model of a human lung, the method comprising steps of preparing a computer file within a computer aided design system utilizing steps of forming a trachea portion having a first end and a second end, forming a first bifurcation zone at the second end of the trachea portion, the first bifurcation zone having a first branch and a second branch, extending a first generation bronchi tube from the first branch of the first bifurcation zone, the first generation bronchi tube having a distal end, forming a subsequent bifurcation zone at the distal end of the first generation bronchi tube, which may be referred to as a prior generation bronchi tube, the subsequent bifurcation zone having a first branch and a second branch, extending a subsequent generation bronchi tube from the first branch of the subsequent bifurcation zone, which may be referred to as a prior bifurcation zone, the subsequent generation bronchi tube having a distal end, repeating the steps of forming a subsequent bifurcation zone at the distal end of the prior generation bronchi tube, the subsequent bifurcation zone having a first branch and a second branch, and extending a subsequent generation bronchi tube from the first branch of the prior bifurcation zone, until a predetermined number of generations of bronchi tubes have been formed, providing the computer file to an additive manufacturing apparatus, fabricating, with the additive manufacturing apparatus, a 3D object based on the computer file, the trachea portion having a sidewall with a thickness, wherein the step of forming a trachea portion includes steps of forming the first end as a circle having a predetermined interior diameter, prescribing a length of the trachea portion as five times the interior diameter of the first end, prescribing a fixed tapering amount for the entire model, which is defined by a decrease from the interior diameter of the first end to an interior diameter of the second end, prescribing a thickness of the sidewall, wherein the steps of prescribing thereby set the length of the trachea portion, the interior diameter of the second end, the thickness of the sidewall, to thereby allow the trachea portion to be formed within the computer aided design system.

12. The method of claim 11, wherein the step of forming a first bifurcation zone includes steps of extending two construction lines from the second end of the trachea portion, where the two construction lines form a total bifurcation angle, extending a perpendicular construction line from a point on each of the two construction lines, each of the perpendicular construction lines extending inward until meeting at a point, dimensioning one of the perpendicular construction lines based on a predetermined value for a radius of the first generation bronchi tube to form a dimensioned perpendicular construction line, and forming a plane along the dimensioned perpendicular construction line.

13. The method of claim 12, wherein the step of extending a first generation bronchi tube includes steps of forming a first circle having a predetermined diameter along the plane along the dimensioned perpendicular construction line, dimensioning one of the construction lines, starting from the point on the construction line and based on a predetermined value for a length of the first generation bronchi tube, to thereby form a dimensioned construction line having a distal point, forming a plane along the distal point of dimensioned construction line, and forming a second circle having a predetermined diameter along the plane along the distal point of dimensioned construction line.

14. The method of claim 13, wherein the length of the first generation bronchi tube is three times the diameter of the first circle.

15. The method of claim 14, wherein the fixed tapering amount is 13.5% percent such that the diameter of the second circle having a predetermined diameter is a 13.5% decrease compared to the diameter of the first circle having a predetermined diameter.

16. The method of claim 11, wherein the diameter of the first end of a particular generation bronchi tube is defined as $d_z = d_0 \times 2^{-z/3}$, where z is the generation number and $d_0$ is the diameter of the first end of the trachea portion.

17. A method of producing a model of a human lung, the method comprising steps of preparing a computer file within a computer aided design system utilizing steps of
    forming a trachea portion having a first end and a second end,
    prescribing a fixed tapering amount for the entire model, which is defined by a decrease from an interior diameter of the first end to an interior diameter of the second end, interior diameter of the second, wherein the fixed tapering amount includes the interior diameter of the second end being decreased by from 13% to 14% compared to the interior diameter of the first end, wherein the fixed tapering amount is applied to the trachea portion and to all subsequent bronchi tubes,
    forming a first bifurcation zone at the second end of the trachea portion, the first bifurcation zone having a first branch and a second branch,
    extending a first generation bronchi tube from the first branch of the first bifurcation zone, the first generation bronchi tube having a distal end,
    forming a subsequent bifurcation zone at the distal end of the first generation bronchi tube, which may be referred to as a prior generation bronchi tube, the subsequent bifurcation zone having a first branch and a second branch,
    extending a subsequent generation bronchi tube from the first branch of the subsequent bifurcation zone, which may be referred to as a prior bifurcation zone, the subsequent generation bronchi tube having a distal end,
    repeating the steps of
        forming a subsequent bifurcation zone at the distal end of the prior generation bronchi tube, the subsequent bifurcation zone having a first branch and a second branch, and
        extending a subsequent generation bronchi tube from the first branch of the prior bifurcation zone,
    until a predetermined number of generations of bronchi tubes have been formed,
    wherein the computer file is adaptable with an additive manufacturing apparatus, providing the computer file to the additive manufacturing apparatus,
    fabricating, with the additive manufacturing apparatus, a 3D object based on the computer file.

18. The method of claim 17, wherein the fixed tapering amount includes the interior diameter of the second end being decreased by 13.5% compared to the interior diameter of the first end.

* * * * *